United States Patent [19]

Ahnell

[11] 4,321,322

[45] Mar. 23, 1982

[54] PULSED VOLTAMMETRIC DETECTION OF MICROORGANISMS

[76] Inventor: Joseph E. Ahnell, 4519 Hydes Rd., Hydes, Md. 21082

[21] Appl. No.: 160,507

[22] Filed: Jun. 18, 1980

Related U.S. Application Data

[63] Continuation-in-part of Ser. No. 49,561, Jun. 18, 1979, abandoned.

[51] Int. Cl.³ .............................................. C12Q 1/04
[52] U.S. Cl. .................................. 435/34; 204/195 B; 204/1T; 435/36; 435/38; 435/39; 435/817
[58] Field of Search ....................... 435/29, 34, 36, 37, 435/38, 39, 40, 817; 204/195 B, 1 E

[56] References Cited

U.S. PATENT DOCUMENTS

| | | | |
|---|---|---|---|
| 2,913,386 | 11/1959 | Clark, Jr. | 204/195 |
| 3,282,803 | 11/1966 | Poepel et al. | 204/1 |
| 3,403,081 | 9/1968 | Rohrback et al. | 204/1 |
| 3,405,030 | 10/1968 | Morter | 162/161 |
| 3,506,544 | 4/1970 | Silverman et al. | 204/1 |
| 3,743,581 | 7/1973 | Cady et al. | 435/34 |
| 3,765,841 | 10/1973 | Paulson et al. | 23/230 B |
| 3,838,034 | 9/1974 | Groves | 204/195B |
| 3,857,771 | 12/1974 | Sternberg | 204/195 B |
| 4,009,078 | 2/1977 | Wilkins et al. | 435/34 |
| 4,085,009 | 4/1978 | Pace | 204/1 T |
| 4,115,230 | 9/1978 | Beckman | 204/195 R |

FOREIGN PATENT DOCUMENTS

| | | |
|---|---|---|
| 231262 | 11/1960 | Australia . |
| 2627633 | 12/1977 | Fed. Rep. of Germany . |
| 2747033 | 4/1978 | Fed. Rep. of Germany . |
| 129579 | 11/1976 | German Democratic Rep. . |

OTHER PUBLICATIONS

Judd R. Wilkins, "Use of Platinum Electrodes for the Electrochemical Detection of Bacteria", Applied and Environmental Microbiology, vol. 36, No. 5 pp. 683–687; 1978.

Matsunaga et al. "Electrode System for the Determination of Microbial Populations", Applied and Environmental Microbiology vol. 37, No. 1 pp. 117–121; 1979.

J. R. Norris and D. W. Ribbons, Methods in Microbiology, vol. II, Chapters 4 and 5, Academic Press, London; 1970.

Irving Fatt, Polarographic Oxygen Sensors, Chemical Rubber Co. Press Cleveland, 1976.

Michael L. Hitchman, Measurement of Dissolved Oxygen, Chapters 5–7, Wiley & Sons, New York; 1977.

Donald H. Phillips et al.,Journal of Biochemical and Microbiological Technology and Engineering, vol. III, No. 3, pp. 261–275; 1961.

*Primary Examiner*—Robert J. Warden

[57] ABSTRACT

Reliable and rapid detection of microorganisms is accomplished in an electroanalytical cell using a pulsed voltammetric detection technique employing the growth medium as the electrolyte and analyte and using simple wire electrodes fabricated from readily available materials. Organism detection occurs as a consequence of the depletion of oxygen in the growth medium/electrolyte caused by aerobic metabolism. Times-to-detection vary with inoculum strength in a predictable fashion, permitting quantification of the organism in question when results are compared to those obtained using known inocula of the same organism. The low duty cycle of the pulsed measurement enables the determination of the relative redox potential in the same cell using the same set of electrodes in order to provide information which may be characteristic of the type of organism being studied.

17 Claims, 34 Drawing Figures

FULLY GROWN E.COLI

SAMPLING AND DILUTION SCHEME

E. COLI

E. CLOACAE

E. CLOACAE

P. MIRABILIS

P. MIRABILIS

P. AERUGINOSA

S. AUREUS

S. BOVIS

S. BOVIS

E. COLI
60% DETECTION LEVEL

E. COLI
Au CATHODE

FIG. 27 P. MIRABILIS Au CATHODE

DATA CORRECTION- E. COLI CONTROL (NO INOCULUM)

MINUTES INCUBATION

E. COLI

PLATED SILVER WIRE ELECTRODES

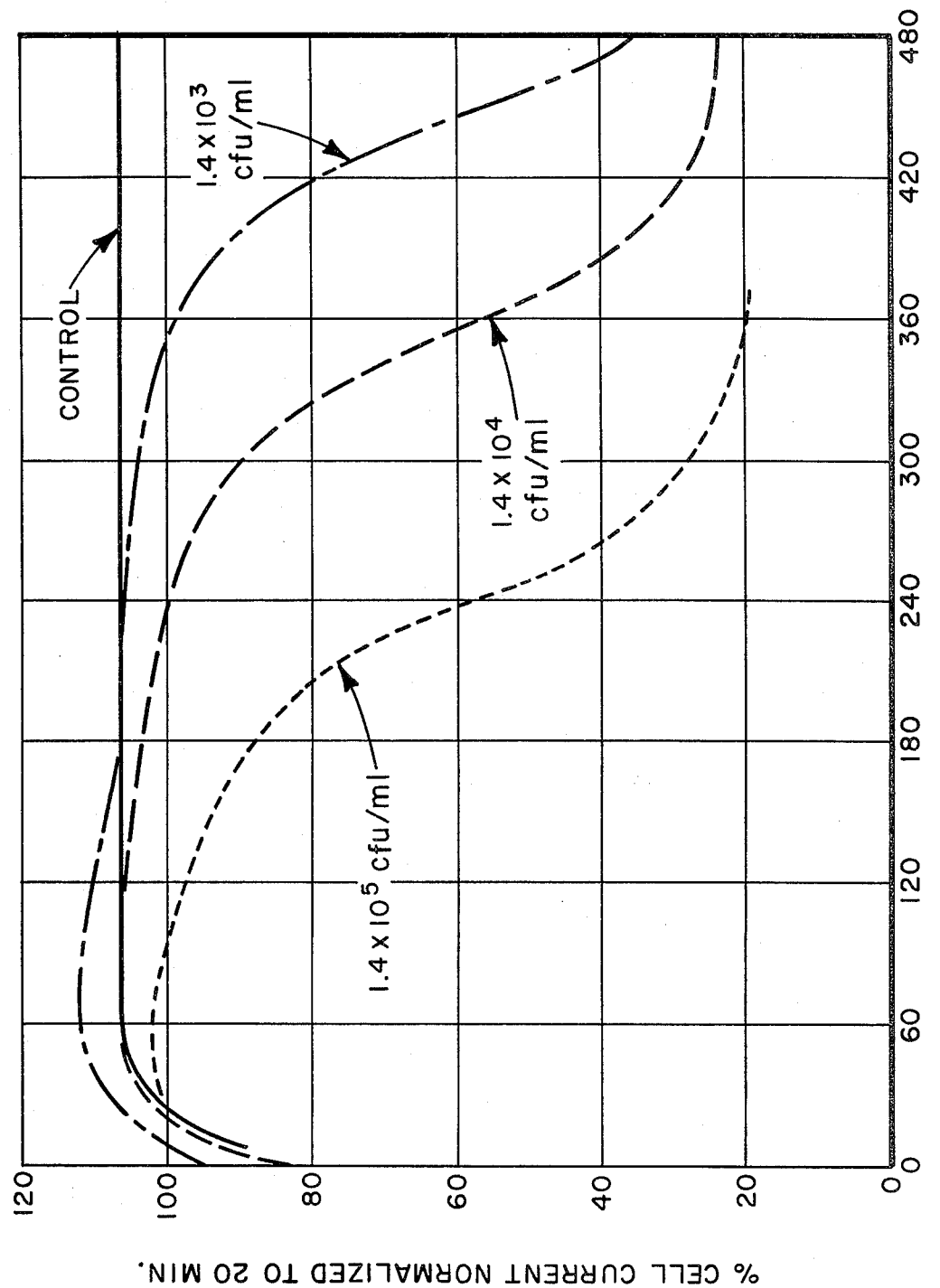

PULSED VOLTAMMETRIC DETECTION OF MICROORGANISMS

This application is a continuation-in-part of copending application Ser. No. 49,561 filed June 18, 1979 now abandoned.

The present invention relates to a method for the detection of microorganisms. More particularly, the present invention relates to a simple, efficient and reliable electrochemical method for the detection of bacteria by measuring the decrease in polarographic oxygen current passing through an electroanalytical cell containing two dissimilar wire electrodes immersed in a liquid culture medium.

The determination of whether or not a substance is contaminated with biologically active agents such as bacteria is of great importance to the medical field, the pharmaceutical industry, the public health field, the cosmetic industry, the food processing industry, and in the preparation of interplanetary space vehicles. One of the most widely used techniques for making this determination, especially in medical applications, has been nutrient agar plating. In this method a microorganism is allowed to grow on an agar nutrient substrate, and the growth of the microorganism is observed, at first visually and thereafter by microscopic examination. This technique, which is most commonly used clinically, requires overnight incubation of plates before results are available.

Another technique widely used for the determination of microorganisms involves supplying a microorganism in a growth medium with carbon-14 labeled glucose or the like. See Waters U.S. Pat. No. 3,676,679 and Waters U.S. Pat. No. 3,935,073. The microorganism metabolizes the radioactive glucose and evolves $C^{14}O_2$, which is sampled and counted. While positive results can be obtained by this radiometric method in a relatively short period of time, this method requires the use of comparatively expensive and complex apparatus and involves the handling of radioactive materials.

The prior art also describes a number of detection techniques based on electrochemical phenomena. Generally these techniques employ very delicate and expensive electronic equipment and are extremely difficult to use in an on-going detection program. One of these described methods involves the measurement of polarographic oxygen current in an electroanalytical cell. Cell current is a function of the dissolved oxygen content of the electrolyte, and the metabolic activity of any oxygen-consuming microorganisms present will, therefore, cause the current values to fall off. For a general discussion of this electroanalytical technique see Hitchman, *Measurement of Dissolved Oxygen* (1977); Fatt, *Polarographic Oxygen Sensors* (1976); and Norris, *Methods in Microbiology* (1970). Modern techniques of polarograpic oxygen measurement rely almost exclusively on the so called Clark-type electrodes which employ a semipermeable membrane to prevent the electrodes from contacting the solution; see Clark U.S. Pat. No. 2,913,386.

The commercially available membrane polarographic oxygen detector (MPOD) is presently used to determine dissolved oxygen in BOD studies, marine ecology, wastewater treatment and the like. The MPOD is usually constructed with an inert cathode material (gold, platinum) and a silver-silver chloride reference electrode, and uses a relatively concentrated (0.3–3.0 M) potassium chloride electrolyte. The electrode areas are relatively large (ca. 1.0 cm$^2$) and are prevented from contacting the solution to be analyzed by a semi-permeable membrane, usually of polyethylene or polytetrafluoroethylene. The potential applied to the electrodes is normally about 0.8 V, cathode negative. This potential must be applied to the MPOD several minutes prior to any use of the detector, and must remain applied throughout the duration of any measurements to be made. The MPOD is thus a "steady-state" device, in that all electrode reactions stabilize at new equilibrium values under the influence of an applied potential constant in time. The steady-state cell current detected under these circumstances is a measure of the dissolved oxygen content of the solution. Because proper electrode operation depends upon diffusion of dissolved oxygen through the membrane to reach the cathode, the solution must be stirred or agitated constantly to prevent the depletion of oxygen from the sample solution in the immediate vicinity of the membrane from affecting the results. Some investigation of MPOD operation under non-steady state or pulsed conditions has been undertaken; see Hitchman, supra, Chapter 6.

The Clark-type polarograph sensors, however, suffer from serious drawbacks which make them undesirable for the detection of microorganisms. These sensors are expensive and cumbersome to use. The relatively high cost of the electrodes precludes the use of a separate electrode for each sample. Thus in order to prevent cross contamination of samples, the electrode surfaces have to be sterilized between samples using a strong bactericide, and then rinsed completely with a sterile rinse solution so as not to kill organisms in or contaminate the contents of the next sample cell tested.

The electroanalytical detection of microorganisms by measurement of oxidation-reduction potential has also been described in the prior art; see generally Norris, supra, Chapter 4. In the redox potential method a platinum electrode in combination with any commonly used reference electrode such as the calomel electrode will evidence an equilibrium potential in growth medium proportional to dissolved oxygen in the medium and to any other oxidation-reduction (electron transport) reactions taking place in the solution. Because this is an equilibrium measurement, a voltmeter with very high input impedance must be used to measure the potential existing between the electrodes so as not to displace the equilibrium as a result of current flow. Microorganisms growing in the medium use oxygen from the solution, and may possibly contribute to other redox reactions which cause the measured potential, usually greater than +100 mV (cathode or platinum positive with reference to the standard calomel electrode) in sterile medium, to shift toward more negative values. Aerobic organisms are able to reduce the solution enough to yield measured potentials of −100 mV to −200 mV (vs. SCE). This is also the range of redox potentials where the voltammetric methods cease to function; the cell current due to dissolved oxygen is by this time very small, and is usually swamped by the residual cell current due to solution impurities and electrode imperfections. Facultative anaerobes, however, may reduce the solution extensively. An exhausted culture of *P. mirabilis* will have reduced the medium in a sealed container to a value of around −550 mV (vs. SCE) before ceasing growth. The redox potential method by itself is not well suited to the detection of bacteria because it is relatively slow and the response will depend on the type of organism being detected.

From the foregoing it is clear that a need exists for a simple rapid and reliable method of detecting the presence of microorganisms in a suspect sample.

Accordingly, it is an object of the present invention to provide a method for detecting the presence of microorganisms which employs apparatus which is relatively simple in both construction and operation and which uses relatively inexpensive non-radiolabeled materials.

It is also an object of the present invention to provide a method for the detection of microorganisms which facilitates computer controlled automation and which can incorporate disposable components.

Further objects of the invention will be apparent from a consideration of the following description.

These and other objects of the invention are achieved by providing an electroanalytical method for detecting the presence of oxygen-consuming microorganisms in a sample comprising the steps of providing a mixture of said sample and a fluid culture medium capable of supporting microorganism growth in an electroanalytical cell equipped with two electrodes which are in contact with said mixture; applying a series of voltage pulses of substantially constant amplitude and duration across said electrodes; and measuring the resulting current prior to the trailing edge of each of said applied voltage pulses; the presence of oxygen-consuming microorganisms being indicated by a decrease in cell current which is a function of the dissolved oxygen content of said mixture.

In a preferred embodiment the present invention also contemplates a process for the detection of microorganisms as described above and additionally comprising measuring the open-circuit voltage potential across said electrodes during the interval between successive applied voltage pulses.

Determination of the dissolved oxygen content of the cell is accomplished by pulsing the electrodes briefly with a known potential (cathode negative) and measuring the resulting current through the cell prior to the trailing edge of the applied voltage pulse. The growth medium in the cell is used as both the analyte and the electrolyte for the determination. The very low duty cycle of the pulse with respect to the overall sampling interval obviates the need for constant agitation or stirring of the sample solution required by conventional steady-state methodology, and permits the same electrodes to be used to determine the relative oxidation-reduction potential in the cell through the measurement of the open-circuit potential existing between the electrodes. Bacterial detection is best accomplished by measuring the decrease in pulsed voltammetric oxygen current, while information characteristic of the type of organism present is best furnished by the relative cell potential determination.

Time-to-detection for all organisms studied vary with inoculum strength in a predictable fashion, permitting accurate quantification of the organism in question when results are compared with times-to-detection obtained using known inocula of the same organism.

The process of the present invention provides numerous advantages compared to traditional manual methodology and present automated systems. This process requires a cell of very simple construction, provides ample opportunity for the creation of disposable, promotes automated quality control, prevents any chance of cross-contamination, and can be configured as an instrument very sophisticated in operation, yet extremely simple to operate.

Figure 31:
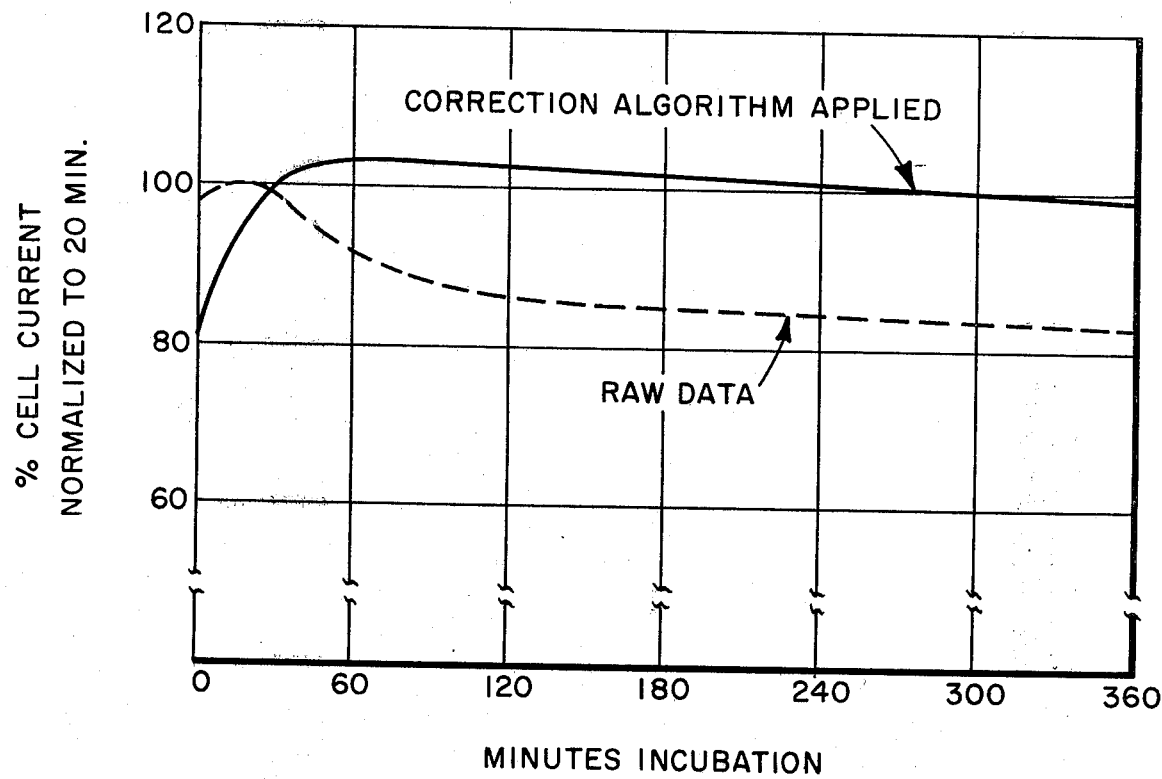

FIG. 31 demonstrates the effect of a data-correcting algorithm upon raw current data from an uninoculated well.

Figure 32:
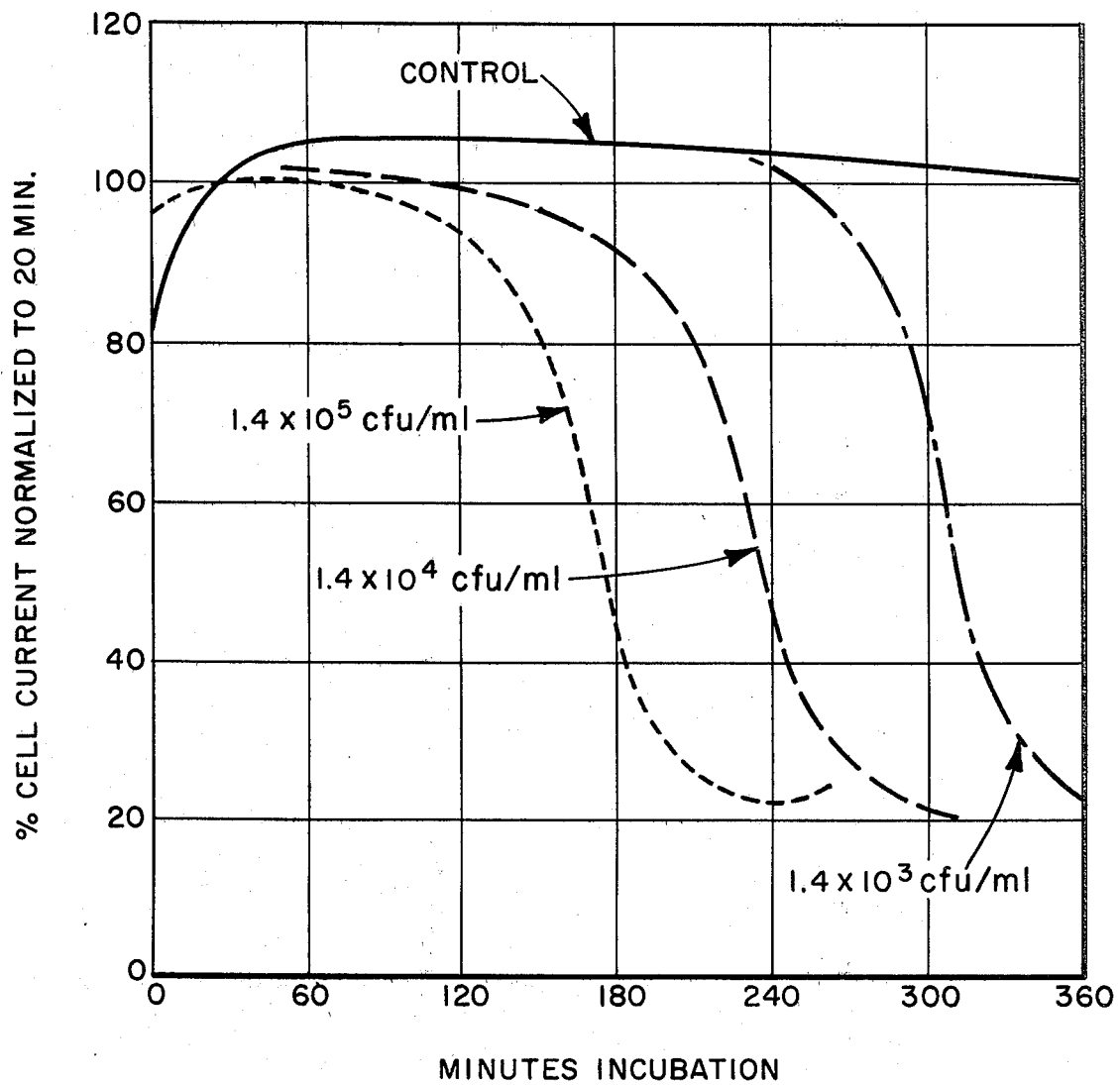

FIG. 32 is a graph showing normalized voltammetric cell current response as a function of incubation time for the organism *E. coli* employing a cell having plated silver wire electrode.

Figure 33:
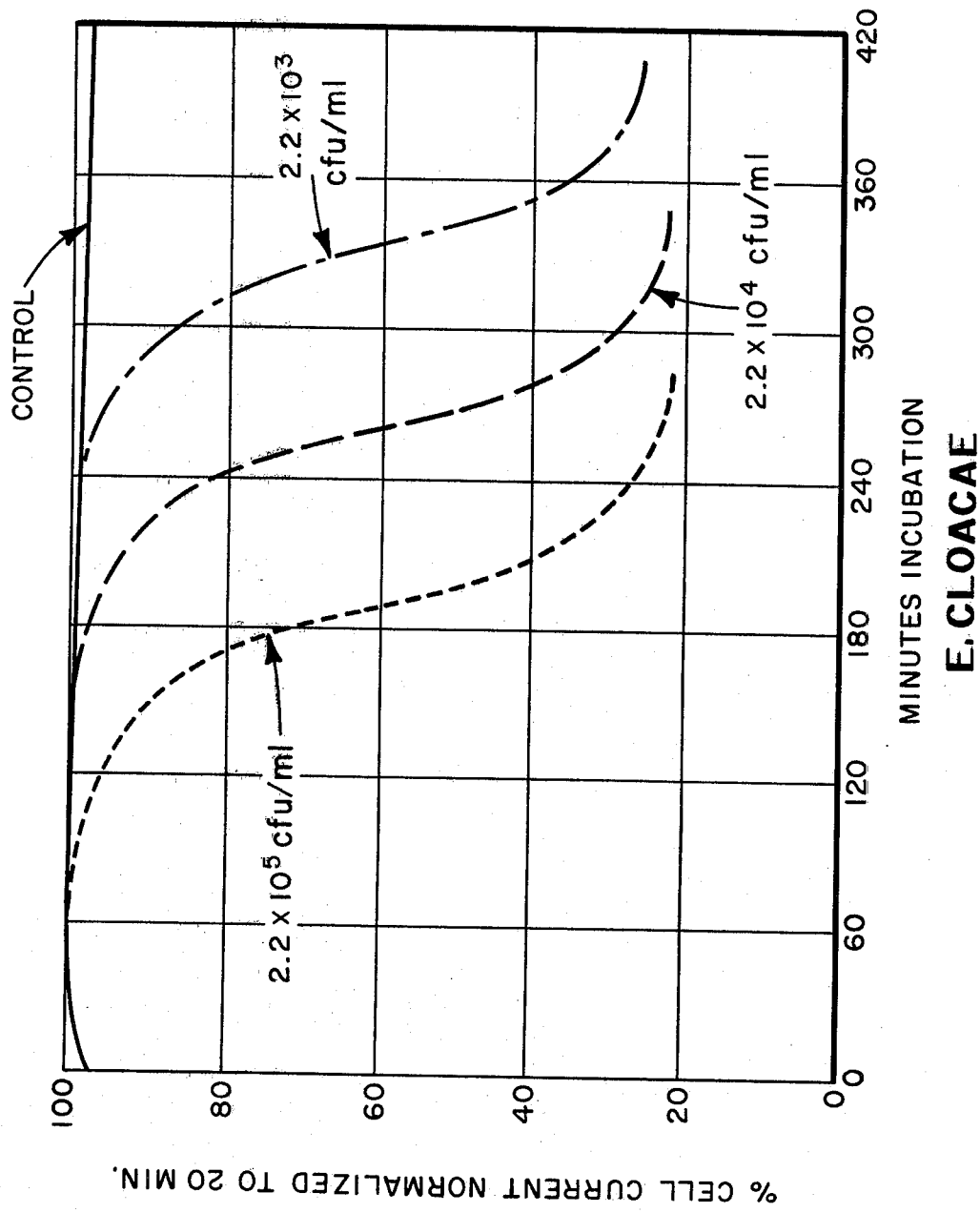

FIGS. 33 and 34 are graphs showing normalized voltammetric cell current response as a function of incubation time for the organisms. *E. cloacae* and *P. aeruginosa* employing cells having plated silver wire electrodes.

The present invention detects the presence of bacteria in a suspect sample primarily by measuring the decrease in voltammetric oxygen current passing through an electroanalytical cell containing the sample and a fluid growth medium. Viable organisms capable of utilizing dissolved oxygen during metabolism will cause the detected oxygen current to decrease with continued incubation, signifying detection. Sterile inocula will evidence no such current decrease. Additional means is provided to measure the open-circuit voltage of the analytical cell in order to obtain information as to the type of bacteria (primarily aerobic or facultative anaerobic) present in the cell. Organisms that consume little or no oxygen from the growth medium, yet which have the ability to alter the solution redox potential, may be detected by noting the change in the solution redox potential with incubation, as furnished by the open-circuit cell potential measurement.

The method of the present invention can be used to detect the presence of any aerobic or facultative organisms which consume oxygen from a liquid medium during metabolism. Specific examples of such organisms include bacteria such as *E. coli, E. cloacae, P. mirabilis, P. aeruginosa, S. aureus, S. bovis, K. peneumoniae, S. albus, K. oxytoca, E. aerogenes, E. agglomerans, C. freundii, P. morganii, P. stuartii, S. marcescens,* Group B. Beta strep, Grp. D. Strep, and yeasts such as *C. albicans*.

In the process of the present invention a small portion of a suspect sample is first introduced into an electroanalytical cell containing a liquid growth medium. The growth medium also serves as the primary electrolyte in the cell. Any medium which will support the growth of oxygen-consuming microorganisms may be utilized.

Typical growth media generally contain water, a carbon source, a nitrogen source, calcium, magnesium, potassium, phosphate, sulfate, and trace amounts of other minor elements. The carbon source may be a carbohydrate, amino acid, mono- or dicarboxylic acid or salt thereof, polyhydroxy alcohol, hydroxy acid or other metabolizable carbon compound. Usually the carbon source will comprise at least one sugar such as glucose, sucrose, fructose, xylose, maltose, lactose etc. Amino acids such as lysine, glycine, alanine, tryrosine, threonine, histidine, leucine, etc. also frequently comprise part of the culture media carbon source.

The nitrogen source may be nitrate, nitrite, ammonia, urea or any other assimilable organic or inorganic nitrogen source. An amino acid might serve as both a carbon and a nitrogen source. Sufficient nitrogen should be present to facilitate cell growth.

A variety of calcium, potassium and magnesium salts may be employed in the growth medium including chlorides, sulfates, phosphates and the like. Similarly, phosphate and sulfate ions can be supplied as a variety of salts. As such materials are conventional in fermentation media, the selection of specific materials as well as their proportions is within the skill of the art.

The so called minor elements which are present in trace amounts are commonly understood to include manganese, iron, zinc, cobalt and possibly others. Due to the fact that most biologically active species cannot function in strongly acidic or strongly alkaline media, suitable buffers such as potassium or ammonium phosphates may be employed, if desired, to maintain the pH of the growth medium near neutrality.

Examples of well known growth media which may be used in the present invention are peptone broth, tryptic soy broth, nutrient broth or thioglycolate broth. Tryptic soy broth-based medium (6B Medium, Johnston Laboratories Inc., Cockeysville, Md.) has been found to work well. The amount of growth medium provided in the electroanalytical cell is not overly critical. 5.0 cc of 6 B medium has proven very effective.

The analytical cell useful in the process of the present invention may be of any convient size and shape. The cell can be formed from any materials normally used in the manufacture of electroanalytical cells such as glass, plastic and the like. Any material which does not affect the growth the microorganisms or the measurement of electrochemical phenomenon in the cell can be employed. In the preferred form, the electronalytical cell useful in the process of the present invention comprise a plastic container of the general configuration shown in FIGS. 1–3. Cell volume may vary according to the cell design and is not critical. A cell of the type shown in FIGS. 1–3 has been effectively used at a capacity of about 10–15 mls. In the preferred manner of operation a number of these cells can be utilized in the form of an array to permit testing of multiple samples.

The electroanalytical cell is also equipped with two electrodes in electrical contact with the growth medium. The working electrode (cathode) is normally a noble metal, for example, gold, silver or platinum.

When only voltammetric measurements are to be taken gold, platinum or silver are preferred for the cathode. When potentiometric (redox) measurements are also taken gold should not be used as the cathode material. When potentiometric measurements are made, dissimilar electrodes are preferred and a platinum cathode and silver anode are particularly preferred. The reference electrode is preferably pure silver (99.95% or better) electrolyzed in place using a basic electrolyte to deposit $Ag_2O$ on the silver. Silver chloride may be electrolytically deposited from HCl solution to form the alternative Ag/AgCl reference electrode, but this electrode has been found less stable in this application. In actual practice clean, unprepared silver wire will quickly become covered with a mixture of $Ag_2O$ and AgCl due to $Cl^-$ ion in the medium and to the very high pH around the anode when pulsed. Although pure silver is known to be bactericidal, no evidence of such toxicity has been noted using oxidized silver reference electrodes. Silver cathodes have also been used without rendering the process inoperative.

Figure 3:
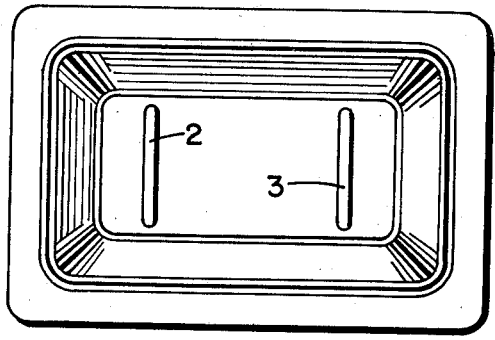
FIG. 3 is a sectional view of the electroanalytical cell of FIG. 1 taken along line 3—3.

The electrodes may be used in any convenient form. Preferred are wires of the above materials although other forms such as printed circuit traces can be used. Most preferred are U-shaped staples inserted through the bottom of the cell as best seen in FIG. 3. The electrodes, however, can be of other conventional forms including spaced apart vartically disposed hairpin shaped electrodes. The electrode wire diameter is not critical. Wires as small as 0.010" may be used, provided their frangibility and low sensitivity can be tolerated. Wires approaching 0.040" probably represent a practical upper limit since these materials are quite expensive. Preferred electrode diameters are in the range of from about 0.015 to 0.050", with about 0.020" to 0.040" being most preferred. Electrode lengths are likewise noncritical. In practice, lengths of from about 0.5 cm to 2.0 cm and preferably about 1.0 to 1.5 cm are suitable. The wires may be separated by about 0.5 to 2.5 cm and preferably about 1.0 to 2.0 cm. It will be apparent to those skilled in the art that solid precious metal wires can be replaced with less expensive wire electroplated with the precious metals of choice.

The electrode pair may be covered with a porous gel, preferably a nutrient gel such as tryptic soy agar (TSA). Other gel materials which may be used include gelatin, dextran gel, carrageenan gel and the like. Best results are obtained when the gel just covers the electrodes. The main benefit of the gel is to reduce measurement baseline drift sometimes caused by the introduction of biological samples (urine, etc.), presumably by preventing the migration of large charged molecules to the electrodes. The quantity of gel is not critical; 1.0 cc of TSA has served to just cover the electrodes in the type of cell shown in FIGS. 1-3. It may be appreciated that some ionic conduction is necessary in the gel; hence its equivalent conductance when saturated with growth medium/electrolyte should approach that of the medium alone.

The electrode pair may also be isolated from the effects of large charged molecules by positioning a layer of porous material such as ordinary filter paper over the electrodes. While this will not prevent contact of the electrodes with the analyte or even with the microorganisms in the sample, it will limit migration of large charged molecules to the electrode region.

In another embodiment of the present invention the reference electrode can be isolated from the analyte mixture by the use of a salt bridge or other conventional means. In this manner it is possible to employ a single reference electrode in conjunction with a plurality of working electrodes in separate analytical half cells.

After the cell has been inoculated with a sample to be tested a series of voltage pulses of substantially constant amplitude and duration are applied across the electrodes. The voltage amplitude of the pulses can vary from about −0.35 v. to about −0.90 v. Preferred is an applied voltage pulse of about −0.70 v. The pulse duration should be at least about 600 milliseconds. The upper limit of the pulse duration is not critical. As a practical matter, times much over about 3 seconds result in a reduced current signal but may be used. Preferably the pulse duration can be from about 800 to 2000 ms. with about 1200 ms. being most preferred. The pulse interval is not critical and should be short enough to follow the biological changes but long enough to allow the cell to approach equilibrium conditions for redox potential measurements in the pulse intervals. Times of from about 5 min. to 20 min. are suitable. A pulse interval of about 10 minutes is preferred.

During the testing period the analytical cell and its contents should be held at a constant temperature, preferably 37° C.±0.2° C. It is understood, however, that not all biologically active agents exhibit maximum growth within the cited temperature range. If it is of interest to determine whether or not a specific microorganism which grows better at some other temperature is present, then the temperature at which the organism in question exhibits maximum growth should be employed.

Current readings from the cell are taken prior to the trailing edge of each of the applied voltage pulses. The pulsed, periodic nature of the measurements involved obviates the need for constant agitation or stirring of the sample as would be required for conventional steady-state polarographic oxygen determination. The requirement of extremely high input impedance for the potential measuring circuitry is similarly relaxed, since the analytical cell is connected to the external electronics only long enough for appropriate potential and current readings to be taken. The simplicity of the analytical cell coupled with the complexities of sample selection and interrogation suggest that the technique of the present invention be practiced in a fully automated fashion. A microcomputer system can be used to control all aspects of experimental measurement and to analyze, tabulate, plot, and store on floppy disk the information gathered during each experiment.

Figure 1:
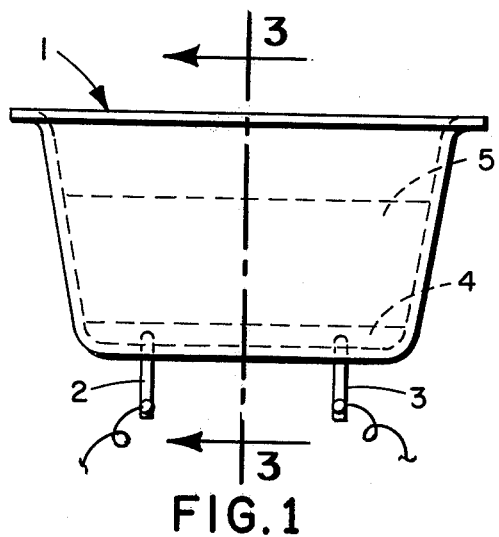
FIG. 1 is a front elevation view of an electroanalytical cell useful in the process of the present invention.
Figure 2:
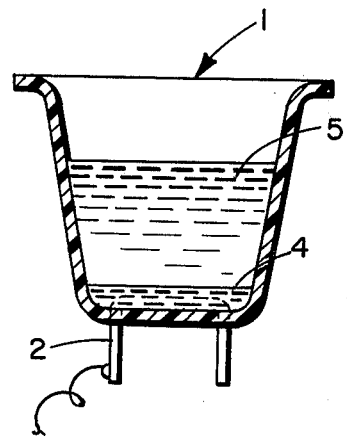
FIG. 2 is a top plan view of the electroanalytical cell of FIG. 1.

The construction of a typical analytical cell useful in the process of the present invention is shown in FIGS. 1-3. A semi-flexible plastic container (1) receives the two wire electrodes (2,3) in the form of U-shaped "staples" inserted through the bottom of the container. The working electrode (2) is analytical-grade platinum, 0.035" diameter. Reference electrode (3) is 0.040" diameter Ag/AgO. The electrode pair is covered with a nutrient gel (4) such as tryptic soy agar (TSA). A quantity of liquid growth medium (5) is also present in the cell to serve as the primary electrolyte and to facilitate the growth of microorganisms.

Figure 4:
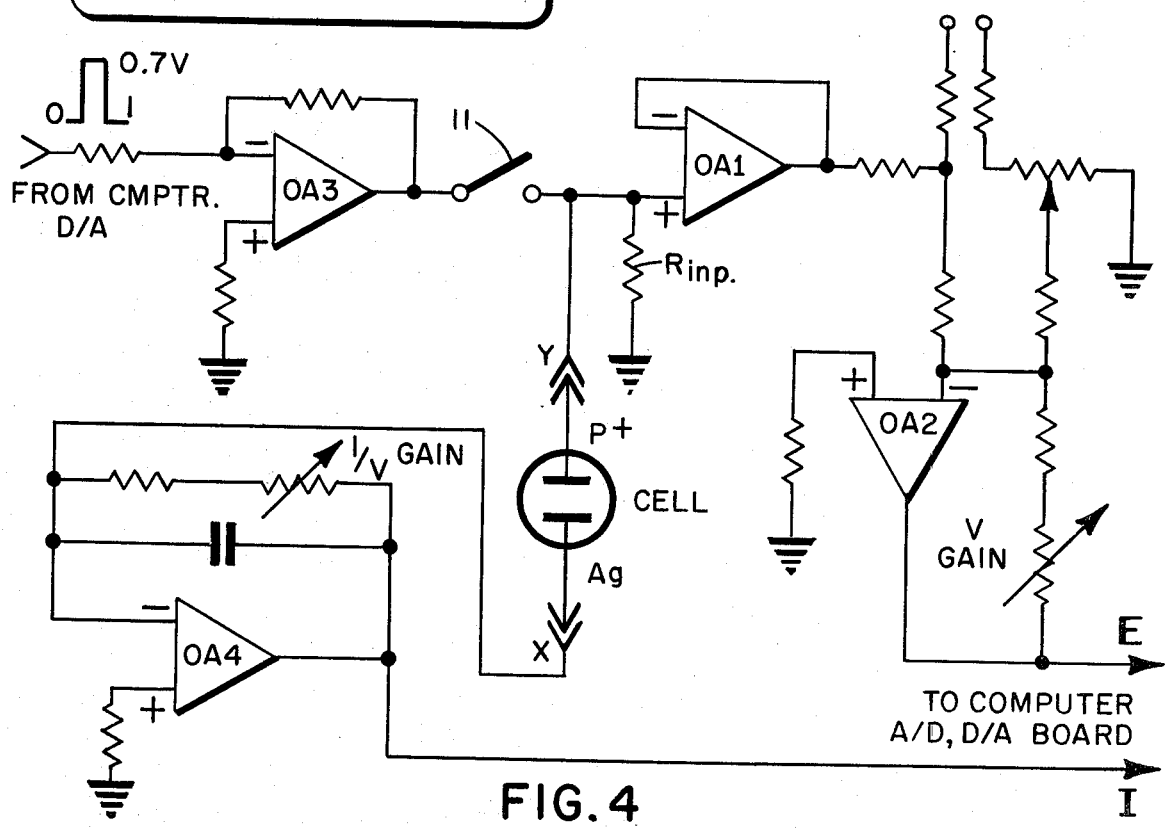
FIG. 4 is a simplified schematic diagram of an analog conditioning circuit useful in the process of the present invention.

The performance of a single experimental data-gathering cycle may be understood by considering a single two-electrode cell as part of the signal conversion circuitry, as presented in simplified form in FIG. 4. A data-gathering cycle begins with the selection of this particular cell. After a short delay to allow the cell selection relays to settle, a potential reading is taken with relay 11 open via operational amplifiers OA1 and OA2. Because the cell redox potentials on platinum are bipolar with respect to the reference electrode (+150 mv to −550 mv) with incubation of a facultative anaerobe, provision is made to offset the potential reading using OA2 to present a unipolar, positive signal of adjustable gain to the computer A/D converter. Immediately following the potential reading, relay 11 closes, and a positive-going pulse derived from the computer D/A converter is applied to OA3. The inverted, unity-gain output of OA3 causes current to flow through the selected cell in proportion to the dissolved oxygen content. The cell current is sensed by OA4, connected as a current-to-voltage converter. The output of OA4 is sampled by a second input of the A/D converter card prior to the termination of the voltage pulse from OA3. All relays are switched off and allowed to settle prior to the selection of the next cell to be tested, at which point the process begins again for the newly selected cell. After all cells have been tested, all relays are deselected while the programmed time interval between readings, usually ten minutes, is allowed to elapse.

The voltage signal input resistor ($R_{inp}$, OA1 in FIG. 4) has the value of 2.2 Megohms. Although this is by no means an electrometric input resistance as is normally employed to measure electroanalytical cell potentials, it must be remembered that the cell is loaded with this resistance for only a few hundred milliseconds before the voltage reading is stored, and that the following voltage pulse drives the cell far from equilibrium in any case. The 2.2 M resistor provides a good compromise between cell loading and noise pickup in the cell environment.

The cell current and potential values measured respectively during and between the successive applied pulses can be compared to the initial values to determine when the threshold of detection has been reached. This process is facilitated by normalization of the collected values as described more fully in Example 2. When the current level has fallen to a predetermined percentage of the initial value, e.g., 60-80%, detection is found to have occurred. It is also possible to make determinations by comparing the collected data to that obtained in a separate reference well.

The method of the present invention can be used in any application where the detection of microorganisms in a sample is desired. This method finds particular utility in the detection of bacteria in biological fluids such as blood, urine and the like.

As will be readily appreciated by one skilled in the art, bacterial testing can include screening, identification, and antibiotic susceptibility testing. Other areas of utility include the detection of microorganism contamination in food, pharmaceutical and cosmetic products.

The following examples are included for illustrative purposes only and are not intended to limit the scope of the invention.

EXAMPLE 1

This example demonstrates the selection of optimum values of the voltage pulse amplitude and duration.

In order to separate the effect of pulse width from that of pulse amplitude in a semi-quantitative fashion, a test was conducted to determine the cell current at various pulse widths for applied voltages ranging from 0.00 V to −1.00 V in steps of 0.05 V in a cell containing a spent culture. As in all examples, the platinum electrode received the pulse, while the reference electrode was held at virtual ground. The current-to-voltage conversion gain was held constant.

A single sample cell of an array consisting of 8 cells as shown in FIG. 1 was prepared using 1.0 cc of molten TSA (90° C.) transferred to the cell via sterile syringe. 5.0 cc of a fully-grown *E. coli* culture in 6B medium (oxygen depleted) was similarly transferred to the cell after the agar had solidified. The cell array was placed in a warm-air incubator at 37° C. and allowed to equilibrate for 40 minutes, at which time readings were begun under computer control. A voltage scan of the cell was obtained and plotted for each chosen pulse width. The interval between pulses was approximately 10 seconds, depending somewhat upon the selected pulse width.

Figure 5:
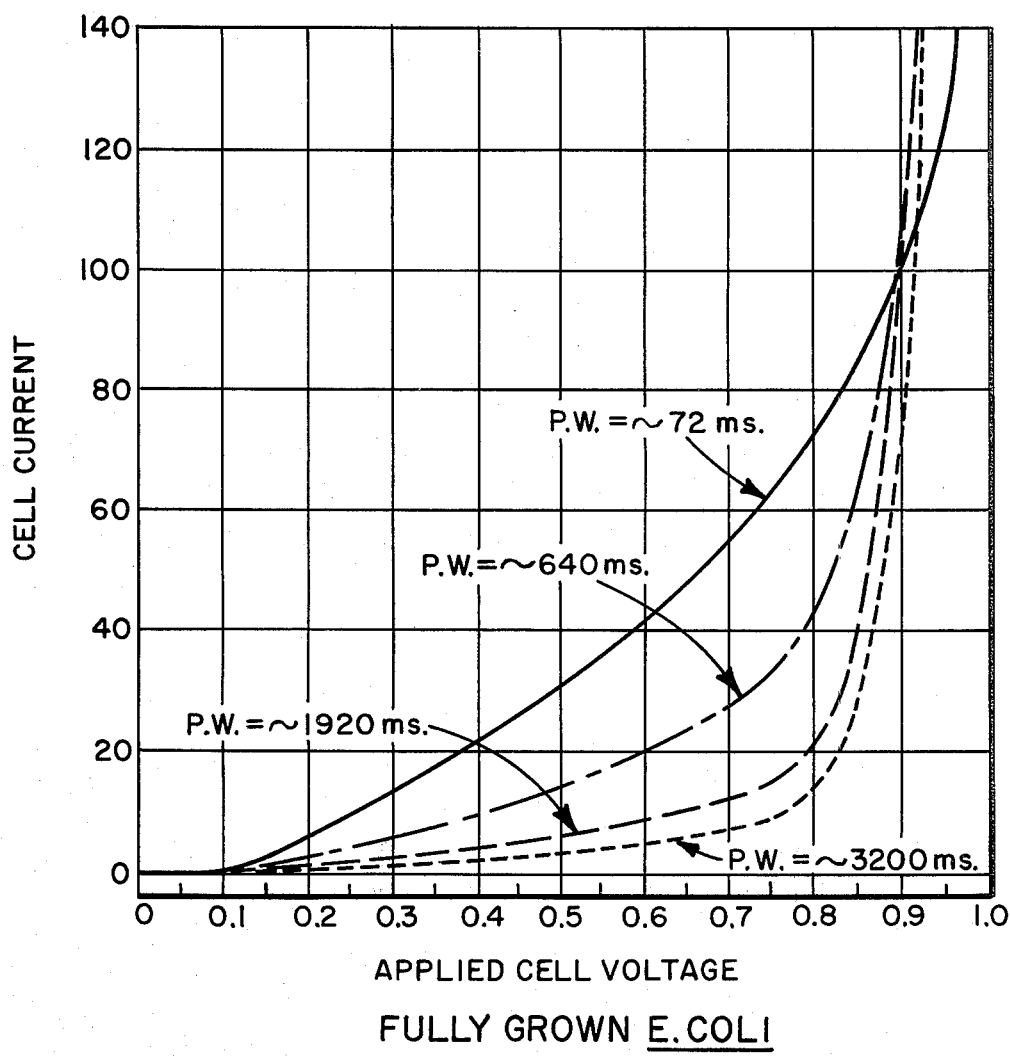
FIG. 5 is graph showing the cell current response of a fully-grown *E. coli* culture at various pulse widths as a function of applied cell voltage.
Figure 7:
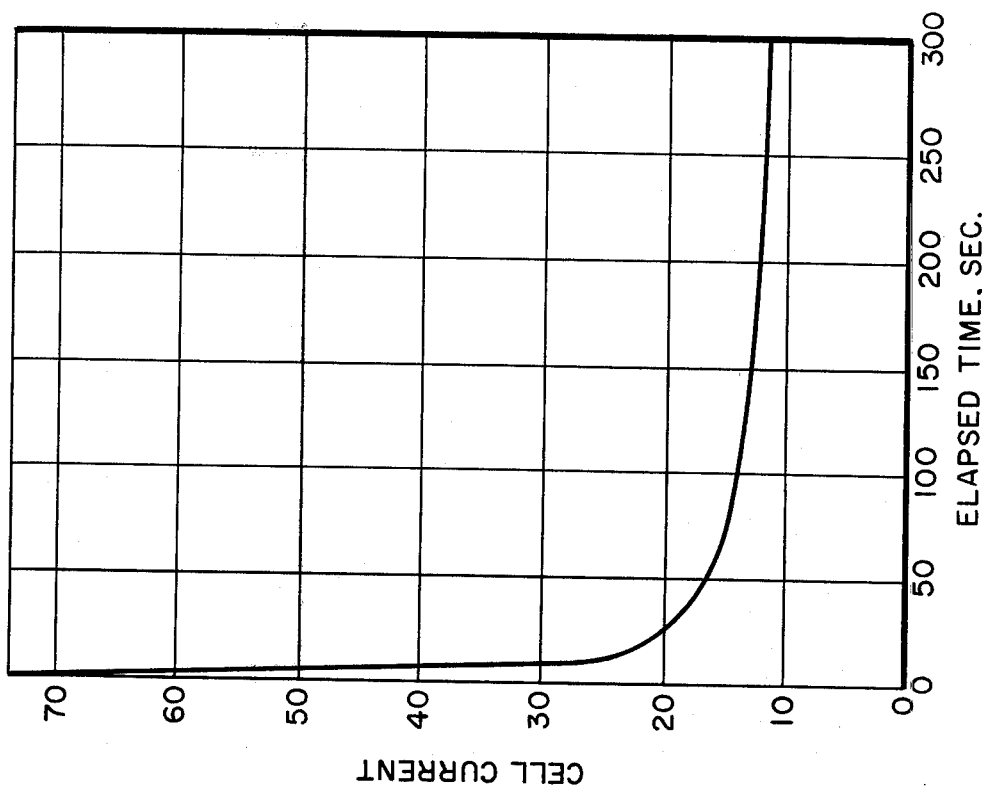
FIG. 7 is a graph showing the cell current response as in FIG. 6 with the elapsed time extended to 300 seconds.
Figure 6:
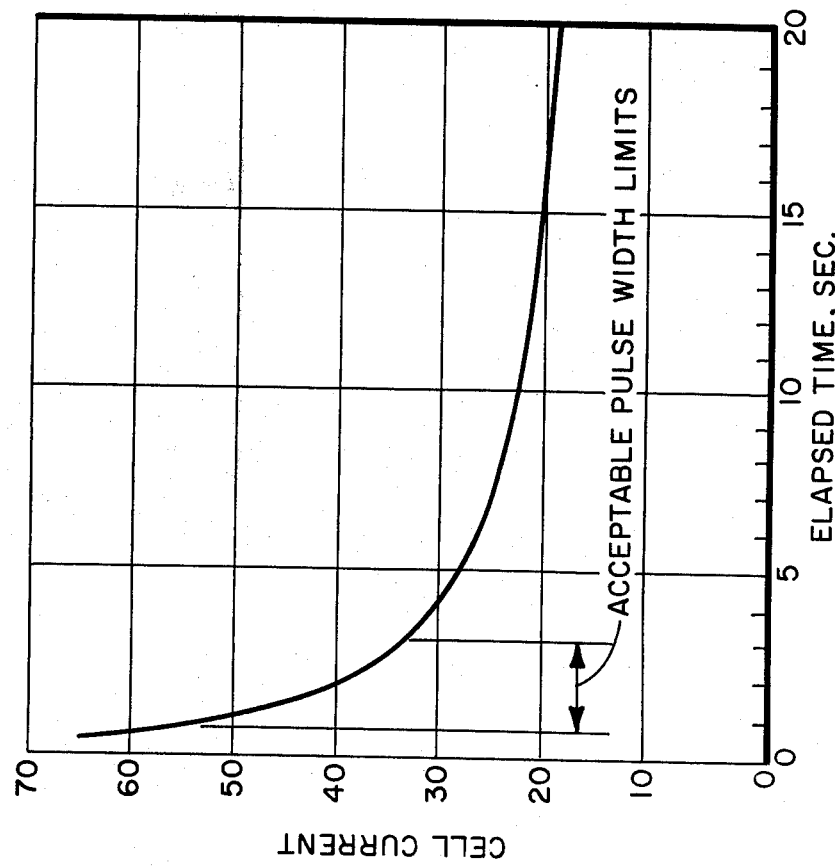
FIG. 6 is a graph showing the cell current response of a sterile cell with constant applied potential as a function of elasped time since pulse application.
Figure 8:
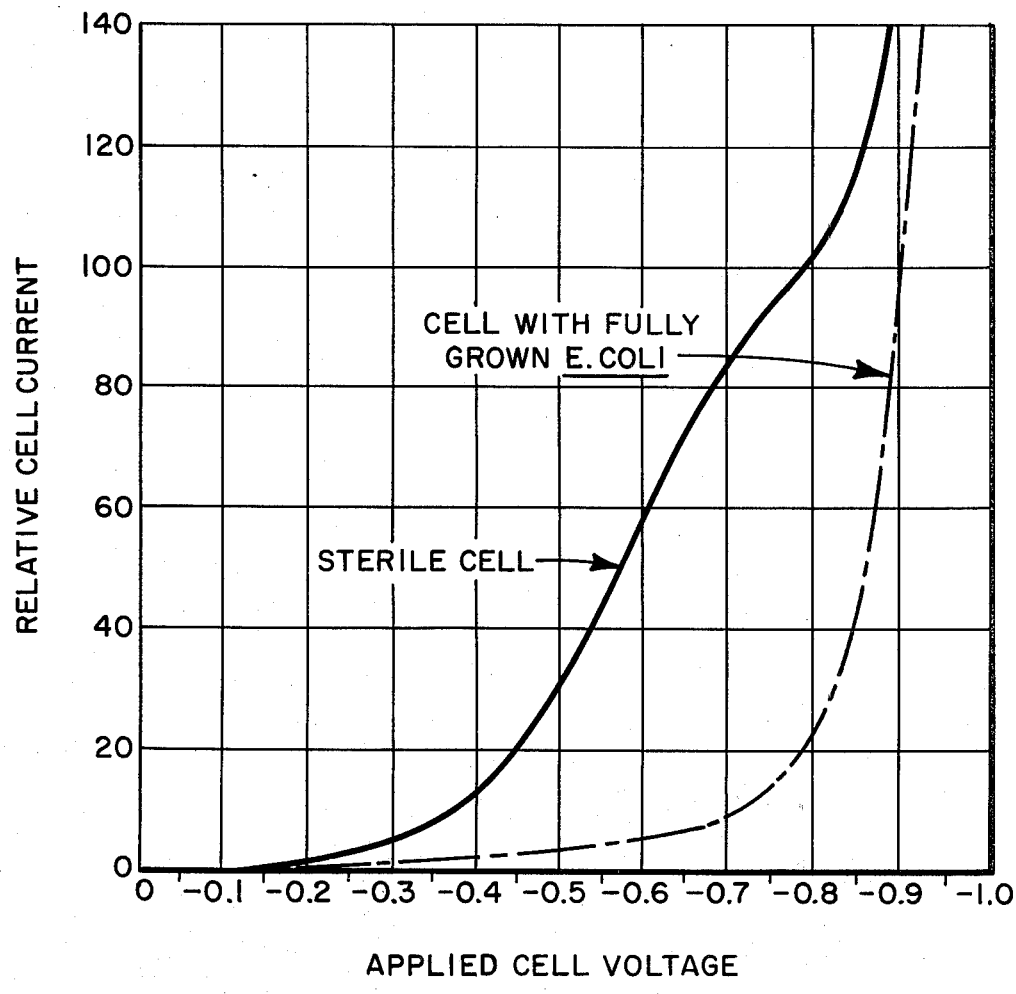
FIG. 8 is a graph showing the cell current response as a function of applied potential for a sterile electroanalytical cell and for a cell containing fully-grown *E. coli* culture.

Cell current responses for selected pulse widths are presented in FIG. 5. It may be noted that the desired cell response is achieved with pulse widths greater than about 640 milliseconds. In practice, pulses of about 1200 ms. duration have been used with good success. Because cell current begins to fall rapidly from the instant the pulse is applied, there is little to be gained from the use of a pulse width in excess of that necessary to produce the desired response. This effect may be noted graphically in FIGS. 6 and 7, which depict the results obtained when a single cell containing 1.0 cc TSA and 5.0 cc 6B medium is subjected to a continuous applied voltage of −0.70 V, with current readings obtained every 0.5 seconds beginning 0.5 seconds after voltage application (FIG. 6). In FIG. 8, one point is plotted for each 20 collected, stored and tabulated. The cell current has decreased to less than half its value at 0.5 seconds (217) after only 4.0 seconds (106); after 5 minutes, cell current has fallen to 16.6% of the initial measurement value (36), yet steady-state conditions have not been achieved. Once the desired cell response of low residual current when containing microbiologically reduced medium has been achieved, further increases in pulse width merely decrease the desired current signal and displace the cell further from thermodynamic equilibrium (FIG. 5). Conversely, pulses shorter than about 600 ms provide unsatisfactory results.

FIG. 8 illustrates a voltage scan overlay for two cells, one containing 1.0 cc of a fully-grown culture of *E. coli* in 6B, the other containing sterile 6B medium, both incubated at 37° C. for 4 hours prior to measurement. A pulse width of about 1300 ms was employed. The cell responses are observed to separate at about −0.35 V, reach maximum divergence near −0.75 V, and converge again about −0.90 V. The detection of microorganisms, then, requires a pulse potential near −0.75 V for best efficiency under these conditions. Consideration of the results presented in FIGS. 5 and 6, together with similar data obtained during the early phases of experimentation led to the selection of −0.70 V as the pulse amplitude, with a width of about 1200 ms for use in the remainder of the examples.

It is also observed that several minutes are required for the cell to return to conditions approaching equilibrium following the application of a voltage pulse. Ideally, the time between pulses should be very large compared to the applied pulse width. Ten minutes was selected as the sampling interval, since it is a short period of time microbiologicaly speaking, yet it provides for a pulse duty cycle of only 0.2% while at the same time permitting the acquisition of semi-continuous data for rapidly growing organisms. Even at this low duty cycle, measured cell potential values are depressed somewhat from their equilibrium values. The measured potentials do, however, adequately represent relative redox potential changes in the growth medium.

Figure 10:
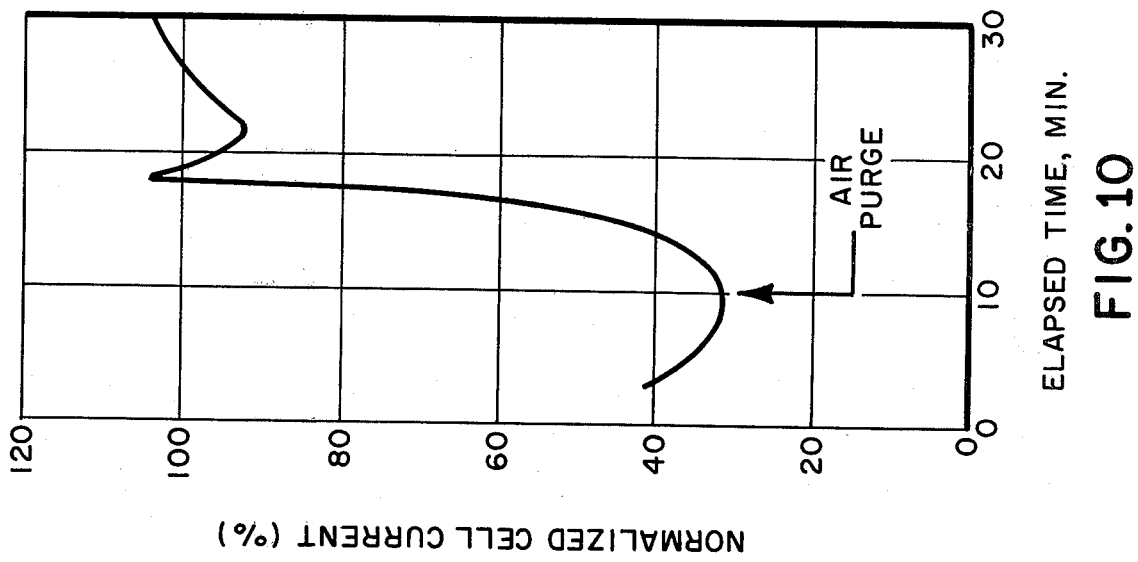
FIG. 10 is a graph showing the cell current response for the sterile cell of FIG. 9 purged with dry nitrogen, then purged with room air.
Figure 9:
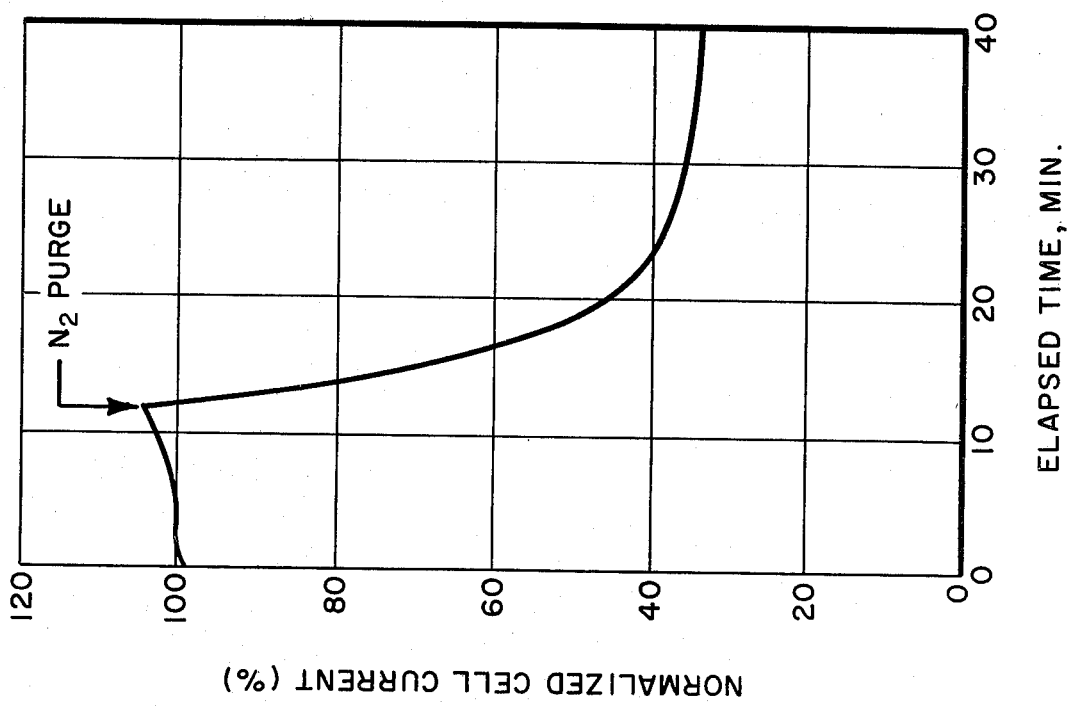
FIG. 9 is a graph showing voltammetric cell current response for a sterile cell purged with dry nitrogen; cell current is recorded as a function of elasped time during the purge.

Finally, in order to insure that dissolved oxygen content is in fact the major parameter determined by the pulse polarographic technique under the chosen experimental conditions, a single cell of the 8-cell array was prepared as usual, containing 1.0 cc TSA and 10.0 cc 6B medium. The cell was incubated at 37° C. for 30 minutes, then ready every 60 seconds for 10 minutes. Dry nitrogen gas (Matheson, High-Purity) was then bubbled through the cell by means of a disposable glass capillary pipette. Readings were continued until the cell current dropped to a reasonably constant value. In a separate experiment conducted in the same cell, nitrogen was again bubbled through the cell, and readings begun just prior to reaching the purge plateau. The gas supply tubing was quickly transferred to a small aquarium pump with flow constrictor, and readings continued for twenty additional minutes. Data from these tests is plotted in FIGS. 9 and 10. Cell response is shown to be clearly related to the oxygen content of the solution; response also appears to be totally reversible in the case of this sterile cell. In actual use with bacteria, however, cell reversibility becomes a strong function of the amount of time the cell is exposed to a fully-grown culture.

EXAMPLE 2

In all the following examples, electrochemical measurements, unless otherwise noted, were carried out in an 8-cell array using platinum (0.035") and silver/silver oxide (0.040") wire electrodes of 1.0 cm length separated by 1.0 cm. Prior to each run, the cells were carefully rinsed with deionized water and vigorously shaken to dislodge the larger droplets. 1.0 cc TSA (Trypic Soy Agar, 40.0 g/l, BBL, Cockeysville, MD) at about 90° C. was then transferred to each cell using a sterile 3.0 cc syringe with 18 ga. needle. The array was then covered, and the agar allowed to solidify. 5.0 cc sterile 6B medium (Johnston Laboratories, Inc., Cockeysville, MD) was then added to each cell, together with 0.1 cc of a 4.5 g/20 ml sterile glucose solution and/or 0.1 cc of a 1.5 g/20 ml sterile glycine solution as desired. The prepared cells were covered and set aside while the inoculum dilutions and pour plate dilutions were prepared.

Fresh cultures of the organisms to be studied were prepared in 6B medium the day before each test, and allowed to incubate at room temperature until needed. Previously prepared sterile 20 cc vials fitted with rubber septa and aluminum closures containing 9.0 cc TSB (27.5 g/l, BBL) were used for all inoculum dilutions. Similar 100 cc vials containing 99.9 cc ½-strength TSB were used to prepare pour plate dilutions. The test was initiated by preparing a sterile 1.0 cc syringe containing about 0.5 cc of the overnight culture of the desired organism. This culture was added dropwise to a 9.0 cc dilution vial with agitation until visual turbidity was achieved. After complete mixing, 1.0 cc was removed from this vial and used to inoculate a second ($\times 0.1$) vial containing 9.0 cc, achieving 1:10 dilution. 1.0 cc from this vial was used to inoculate a third ($\times 0.01$) vial, which was in turn used to inoculate a fourth ($\times 0.001$). Additionally, 0.1 cc was removed from the $\times 1.0$ vial and used to inoculate one 99.9 cc vial to obtain 1:1000 dilution for pour plate preparation. Similarly, 0.1 cc was withdrawn from the $\times 0.01$ vial and used to inoculate a second 99.9 cc vial to obtain 1:100,000 dilution. A fifth vial containing 9.0 cc TSB was used as the source of sterile, control inocula.

1.0 cc of the $\times 1.0$ vial was then transferred to cell (1) of the array. Cells (2) and (3) received 1.0 cc each from the $\times 0.1$ dilution vial; cells (4) and (5) were inoculated with 1.0 cc from the $\times 0.01$ vial, while cells (6) and (7) each received an inoculum from the $\times 0.001$ vial. Cell (8) was inoculated with 1.0 cc sterile TSB to serve as the control.

The inoculated cells were placed in a warm-air incubator held at 37° C.±0.2°, connected to the analog conditioning electronics, and the measurements begun. No preinoculation incubation of the array was employed. Cell current and cell potential readings were obtained at 10-minute intervals using a pulse amplitude of −0.70 V and a pulse duration of 1200 milliseconds.

Figure 11:
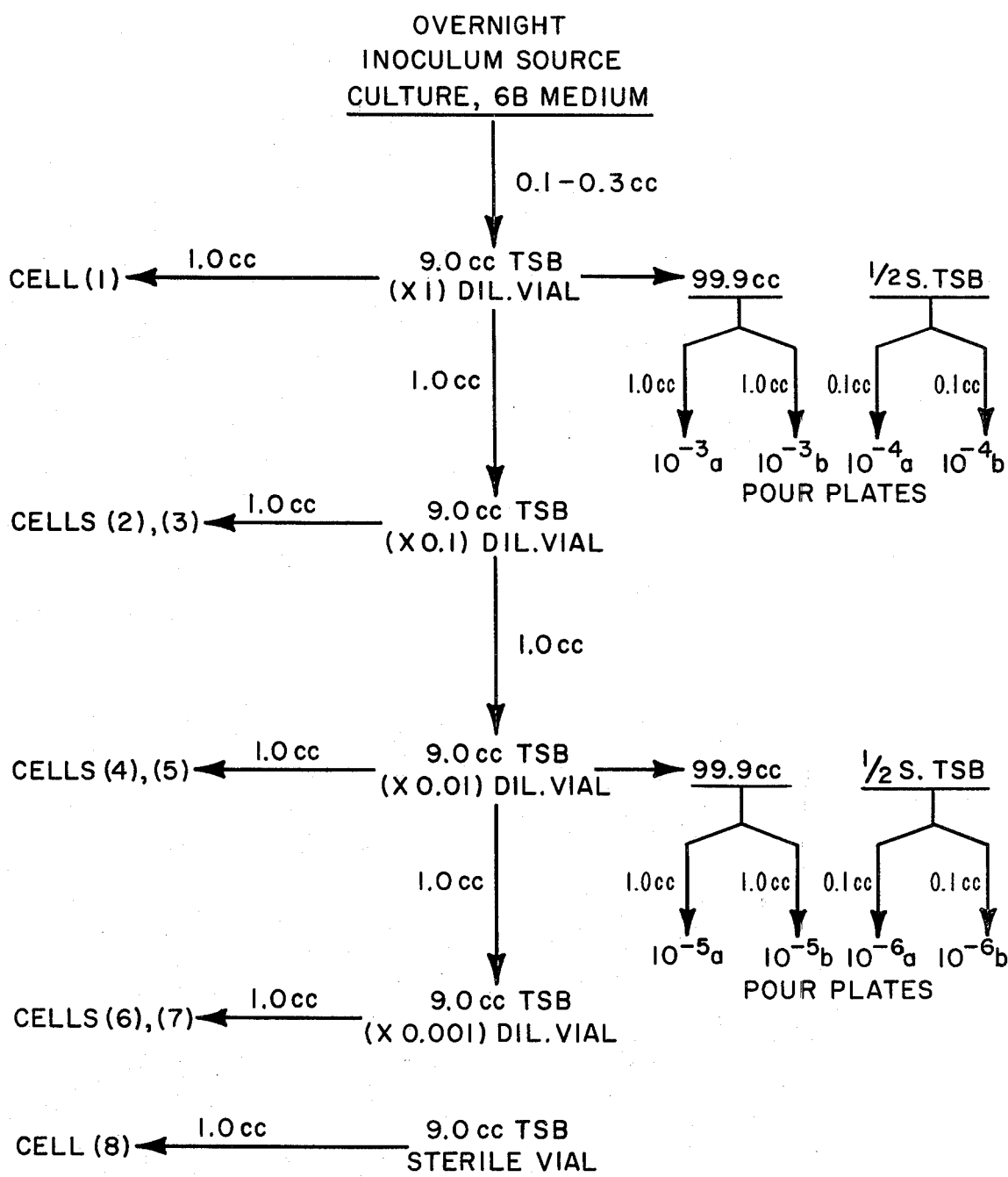
FIG. 11 is a schematic representation of the sampling and dilution scheme used in the preparation of electroanalytical cells and pour plates for the examples.

Duplicate pour plates were prepared containing 10–15 ml TSA (40 g/l) using 1.0 cc and 0.1 cc from each of the 99.9 cc dilution vials to yield pairs of plates at $1:10^3$, $1:10^4$, $1:10^5$, and $1:10^6$ dilutions. The plates were allowed to harden at room temperature prior to 24-hour incubation. Details of the sampling and dilution scheme are set out in FIG. 11.

All values of current and potential recorded by computer in these examples range from 0 to 255 as a consequence of unipolar 8-bit conversion of the input signals. These raw data values are stored in the appropriate memory array during the experiment. All data manipulation is performed after the experiment is terminated. Raw data and experimental specifics are stored on a floppy disk for future retrieval.

Cell current I(T,N) as a function of time (T) and sample number (N) is normalized at a chosen time interval T1 for sample N by dividing cell currents observed at all times T for sample N by the cell current value observed at time T=T1, and then multiplying by 100.0, e.g.:

$$X(T,N) = \frac{I(T,N)}{I(T1,N)} \times 100.0$$

The same normalization time (T1) is used for all samples. The normalized current values X(T,N), now ranging nominally from 0 to 100, are then scaled for plotting through division by a scale factor, herein 2.0, so that all data together with the machine-generated coordinate time axis will fit on the 80-character CRT/printer line. Cell currents for each sample are thus easily presented as a percentage of the normalized current value, usually taken as the current value observed after 30 minutes experiment time.

Cell potential results V(T,N) are normalized by simple Y-axis translation and uniform scaling. A constant is first derived from the voltage observed at the normalizing time interval T1:

$$C = V(T1,N) - 20$$

which is in turn used to translate all observed voltage values for a given sample N:

$$Z(T,N) = V(T,N) - C$$

The translated values Z(T,N) are then scaled to page width by dividing by the scale factor, herein 3.5, and then printed. Potential normalization is usually performed at 60–100 minutes after the experiment has begun. Cell potential readings require about 60 minutes longer, on average, to stabilize than do the current readings.

For the purposes of the following examples, detection of the organism is said to occur when the pulse voltammetric cell current has fallen to 80% of its value at the normalization time interval. Potential measurements are considered positive when a relative normalized value of 20 is attained. All values obtained for cell (1) were used as high-inoculum markers only, and do not appear in the results.

This example demonstrates the detection and quantification of E. coli. A fresh overnight culture of E. coli in 6B medium was used as the inoculum source. The sampling and dilution scheme of FIG. 11 was employed to prepare sample cells and pour plates. The sample cell medium was enriched with 0.1 cc (of the) 4.5 g/20 ml glucose stock solution. Incubation of all vials, sample cells and plates was at 37° C. Cell readings were continued for 8 hours.

Figure 12:
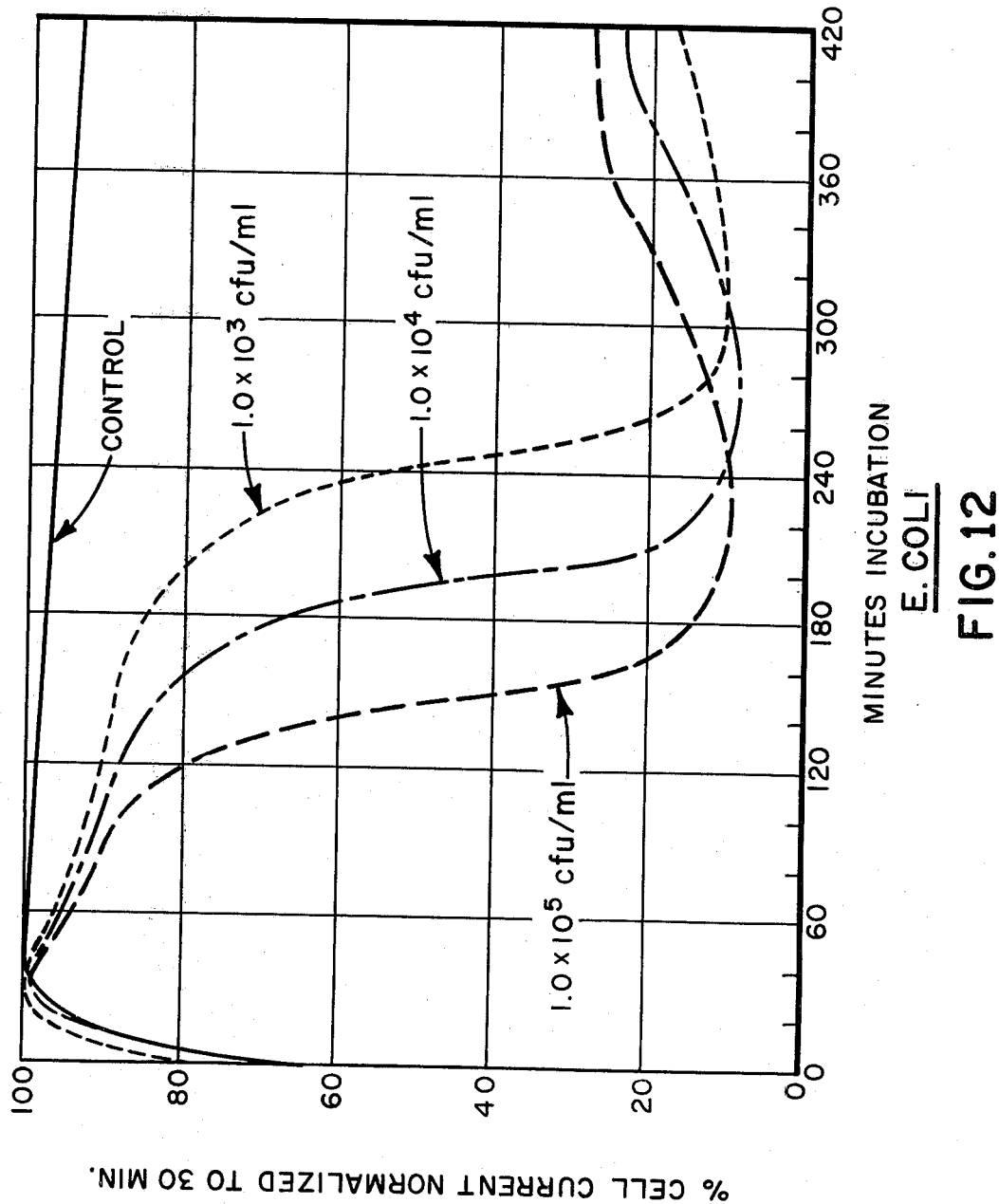
FIG. 12 is a graph showing normalized voltammetric cell current response as a function of incubation time for varying inoculum strengths of the organism *E. coli*.
Figure 13:
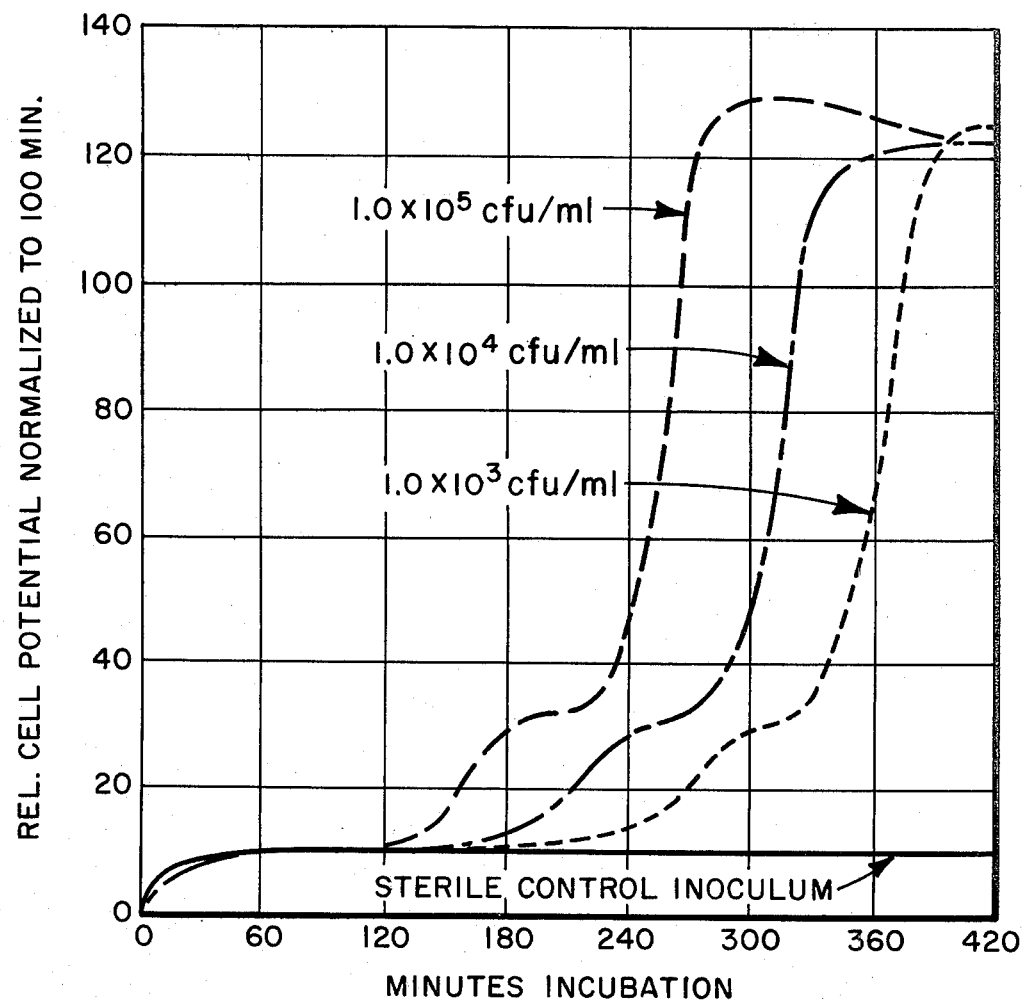
FIG. 13 is a graph showing normalized cell potential response as a function of incubation time for varying inoculum strengths of the organism *E. coli*.

Pulsed voltammetric current responses for three decade dilutions of the organism plus control are shown in FIG. 12. The related cell potential results are presented in FIG. 13. The Y-axis indicates potential increasing in the negative direction. The short plateau evidenced at relative potential values of 30–40 probably indicates a change in the metabolism of the organism triggered by the reduced oxygen tension in the medium. Both cell parameters give times-to-detection which vary in a predictable manner with inoculum strength. Pour plate results indicate that $1.0 \times 10^5$ cfu/ml E. coli were present in the freshly inoculated $\times 0.1$ cell. Times-to-detection for the duplicate cell current and potential measurements are presented in Table 1.

TABLE 1

Times-to-Detection in Minutes for Cell Current and Cell Potential for the Organism E. coli

| Initial Inoculum in Cell | Cell Current | | Cell Potential | |
|---|---|---|---|---|
| | A | B | A | B |
| $1.0 \times 10^5$ cfu/ml | 120 | 120 | 160 | 180 |
| $1.0 \times 10^4$ cfu/ml | 150 | 160 | 220 | 230 |
| $1.0 \times 10^3$ cfu/ml | 200 | 200 | 260 | 270 |

EXAMPLE 3

This example demonstrates the detection and quantification of E. cloacae. A fresh culture of E. cloacae was incubated overnight at room temperature to serve as the inoculum source. The sampling and dilution scheme presented in FIG. 11 was used to prepare duplicate sample cells and pour plates. The cell medium was enriched with 0.1 cc glucose stock solution. All incubations were performed at 37° C. The inoculated cell array was covered with clean aluminum foil, placed in the incubator, and connected to the analog conditioning electronics moments before the start of the test. The test was continued for 520 minutes (8⅔ hours).

Figure 14:
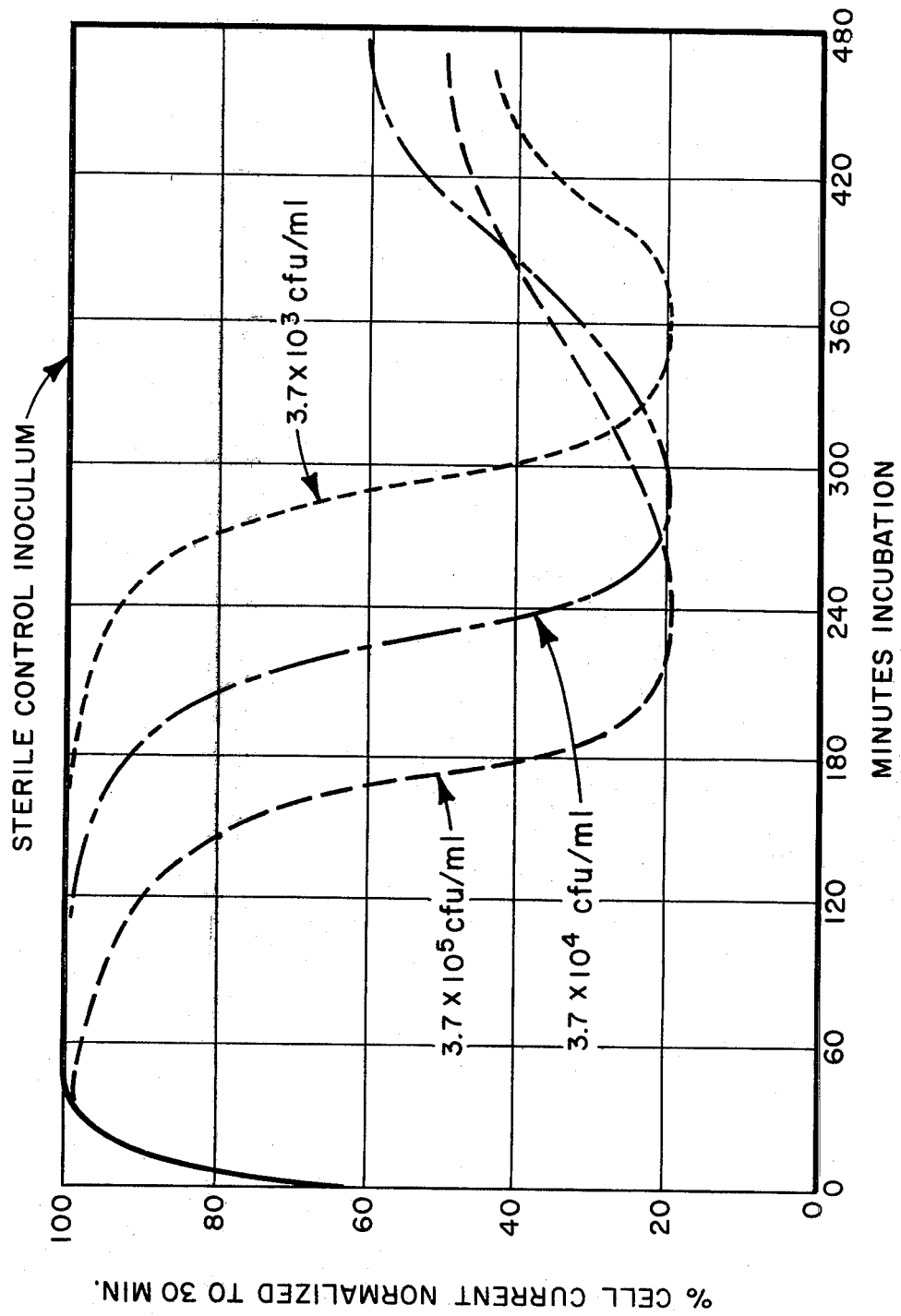
FIG. 14 is a graph showing normalized voltammetric cell current response as a function of incubation time for varying inoculum strengths of the organism *E. cloacae*.
Figure 15:
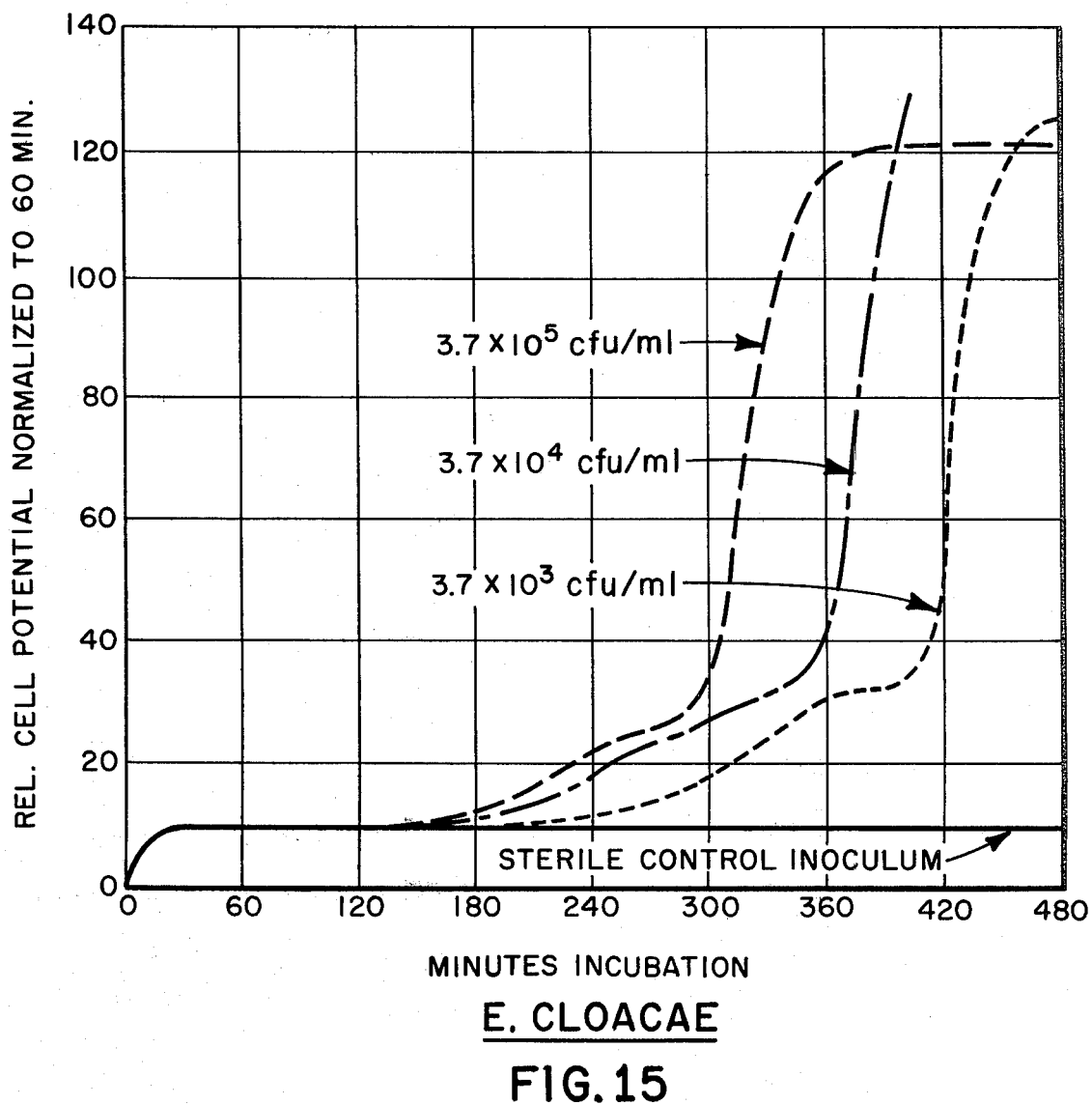
FIG. 15 is a graph showing normalized cell potential response as a function of incubation time for varying inoculum strengths of the organism *E. cloacae*.

The cell current response for each of the three decade dilutions of E. cloacae plus control is presented in FIG. 14. Cell currents are seen to rise relatively rapidly from their attained minimum values probably as a consequence of electrode-active metabolic products synthesized by the organism in its latter stages of growth under reduced conditions. The related cell potential data is shown in FIG. 15. A short plateau in redox potential values is again noted at relative normalized values between 30 and 40, again attributed to an organism metabolic pathway change. Duplicate pour plate counts were used to determine the initial inoculum level in the $\times 0.1$ cells to be $3.7 \times 10^5$ cfu/ml. The incubation times required to detect the organism are listed in Table 2.

TABLE 2

Times-to-Detection in Minutes for Cell Current and Cell Potential for the Organism E. cloacae

| Initial Inoculum in Cell | Cell Current | | Cell Potential | |
|---|---|---|---|---|
| | A | B | A | B |
| $3.7 \times 10^5$ cfu/ml | 150 | 150 | 230 | 200 |
| $3.7 \times 10^4$ cfu/ml | 210 | 210 | 260 | 240 |
| $3.7 \times 10^3$ cfu/ml | 270 | 270 | 300 | 310 |

EXAMPLE 4

This example demonstrates the detection and quantification of P. mirabilis. A fresh overnight culture of P. mirabilis in 6B medium was used as the inoculum source. Sample cells and pour plates were prepared as per the sampling and dilution scheme presented in FIG. 11. 5.0 cc 6B medium was enriched with 0.1 cc sterile glucose stock solution in each of the cells. All incubations were performed at 37° C. The electroanalytical measurement was begun immediately following cell inoculations without preinoculation incubation, and was continued for 540 minutes (9 hrs).

Figure 16:
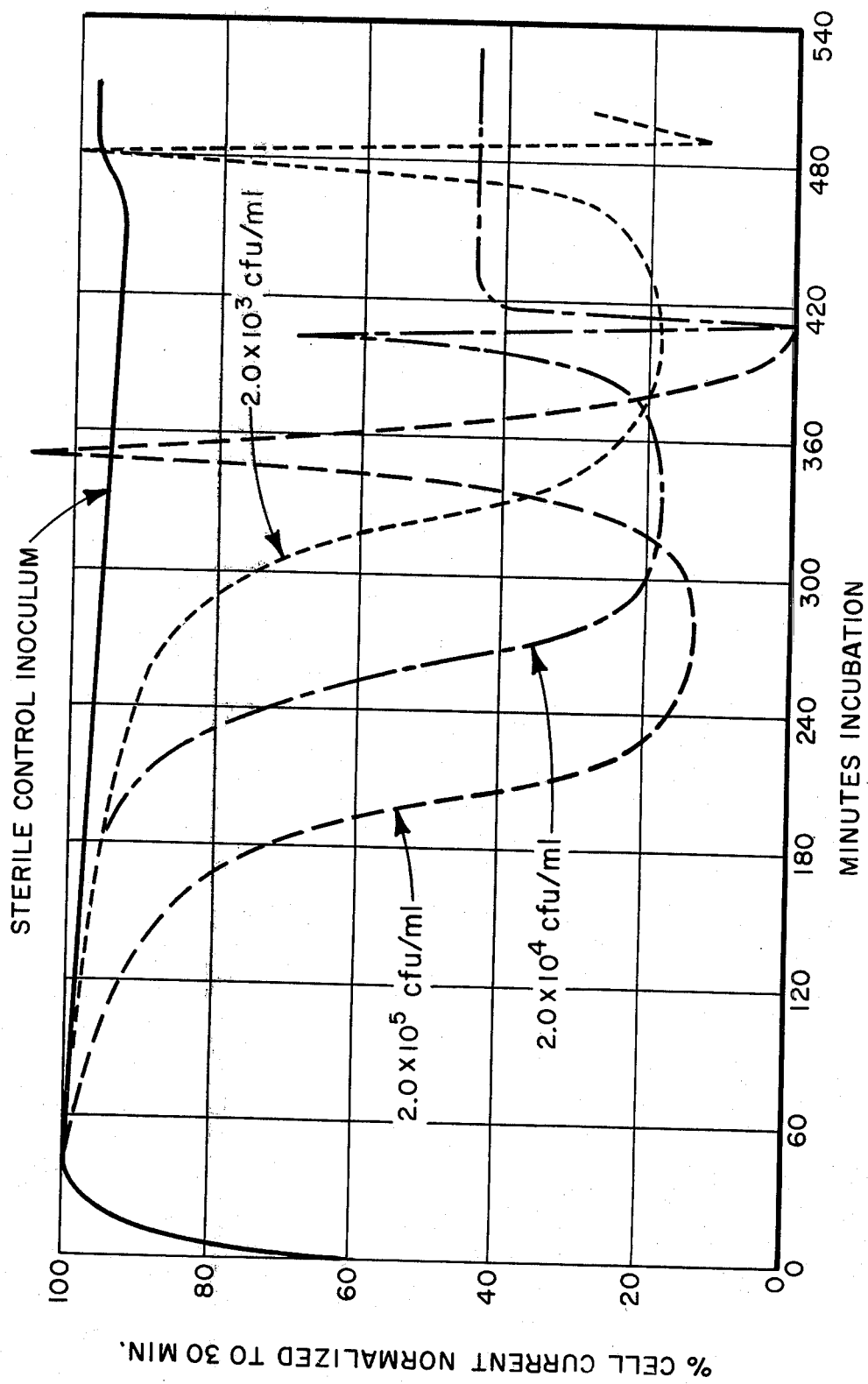
FIG. 16 is a graph showing normalized voltammetric cell current response as a function of incubation time for varying inoculum strengths of the organism *P. mirabilis*.

Pulsed voltammetric cell current responses for the three decade dilutions of the organism are presented in FIG. 16. Cell responses appear normal as oxygen is consumed and cell current falls to the residual level, then rapid vertical transitions appear lasting only 20–30 minutes. Cell current values seem to stabilize following these events, but do not return to pre-transition levels.

Figure 17:
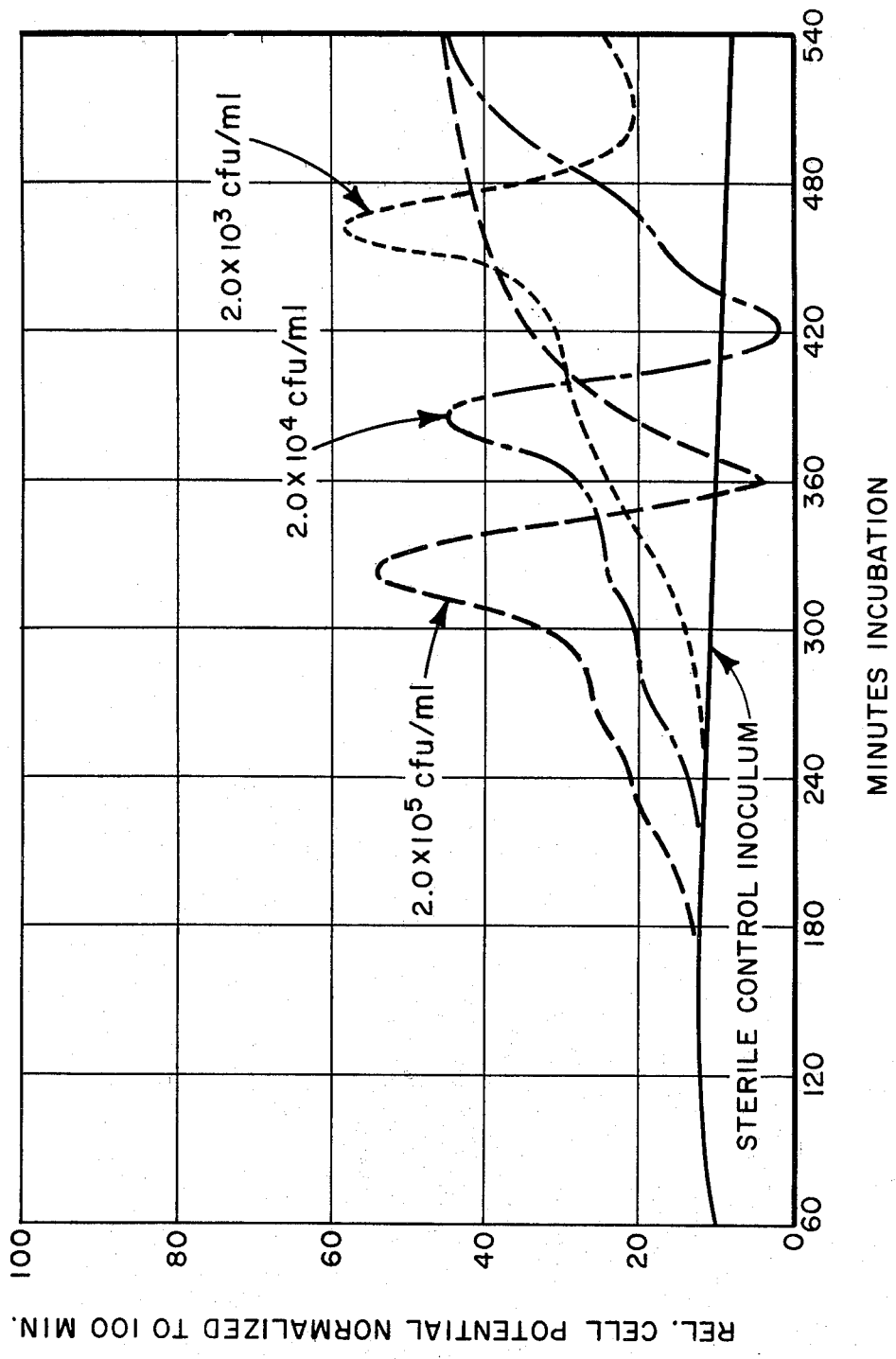
FIG. 17 is a graph showing normalized cell potential response as a function of incubation time for varying inoculum strengths of the organism *P. mirabilis*.

Cell potential responses are shown in FIG. 17. Again, a slight plateau is observed at normalized relative potentials between 30 and 40 units. Instead of the rapidly increasing negative potentials noted for E. coli and E. cloacae, P. mirabilis potentials fall sharply after a slight increase following the plateau. The time intervals noted for this potential decrease correlate well with the observed vertical transitions in cell current previously noted. Since P. mirabilis is a facultative organism known to efficiently reduce growth media, and has been used as a standard organism for medium reduction measurements, these anomalous results in the long-incubation regime are best explained by the formation of electrode-active metabolic by-products, most probably sulfide-containing molecules ($H_2S$, $CH_3SCH_3$, $CH_3SCH_2CH_3$ etc.) which certainly would perturb the electrode system. The silver/silver oxide electrode is noticeably blackened by exposure to P. mirabilis for extended periods. The electrodes do not seem to be permanently damaged by such exposure, and may be returned to their initial condition by careful washing and wiping of the electrode surfaces. The discoloration can be removed only by mechanical polishing. The $\times 0.1$ cells (2) and (3) contained $2.0 \times 10^5$ cfu/ml of P. mirabilis at inoculation as determined by duplicate pour plate counts. Times-to-detection for cell current and cell potential are listed in Table 3.

TABLE 3

Times-to-Detection in Minutes for
Cell Current and Cell Potential
for the Organism *P. mirabilis*

| Initial Inoculum | Cell Current | | Cell Potential | |
|---|---|---|---|---|
| in Cell | A | B | A | B |
| $2.2 \times 10^5$ cfu/ml | 190 | 170 | 250 | 230 |
| $2.0 \times 10^4$ cfu/ml | 220 | 230 | 270 | 280 |
| $2.0 \times 10^3$ cfu/ml | 290 | 300 | 340 | 330 |

EXAMPLE 5

This example demonstrates the detection and quantification of *P. aeruginosa*.

A freshly inoculated vial of 6B medium was incubated overnight at room temperature for use as the source of inocula. The sampling and dilution scheme illustrated in FIG. 11 was employed to prepare sample cells and pour plates. The sample cell medium was enriched with 0.1 cc sterile 1.5 g/20 ml glycine stock solution in each cell. All cells and plates were incubated at 37° C. Electroanalytical cell readings were begun immediately after inoculation and were continued for 490 minutes (8-1/6 hours).

Figure 18:
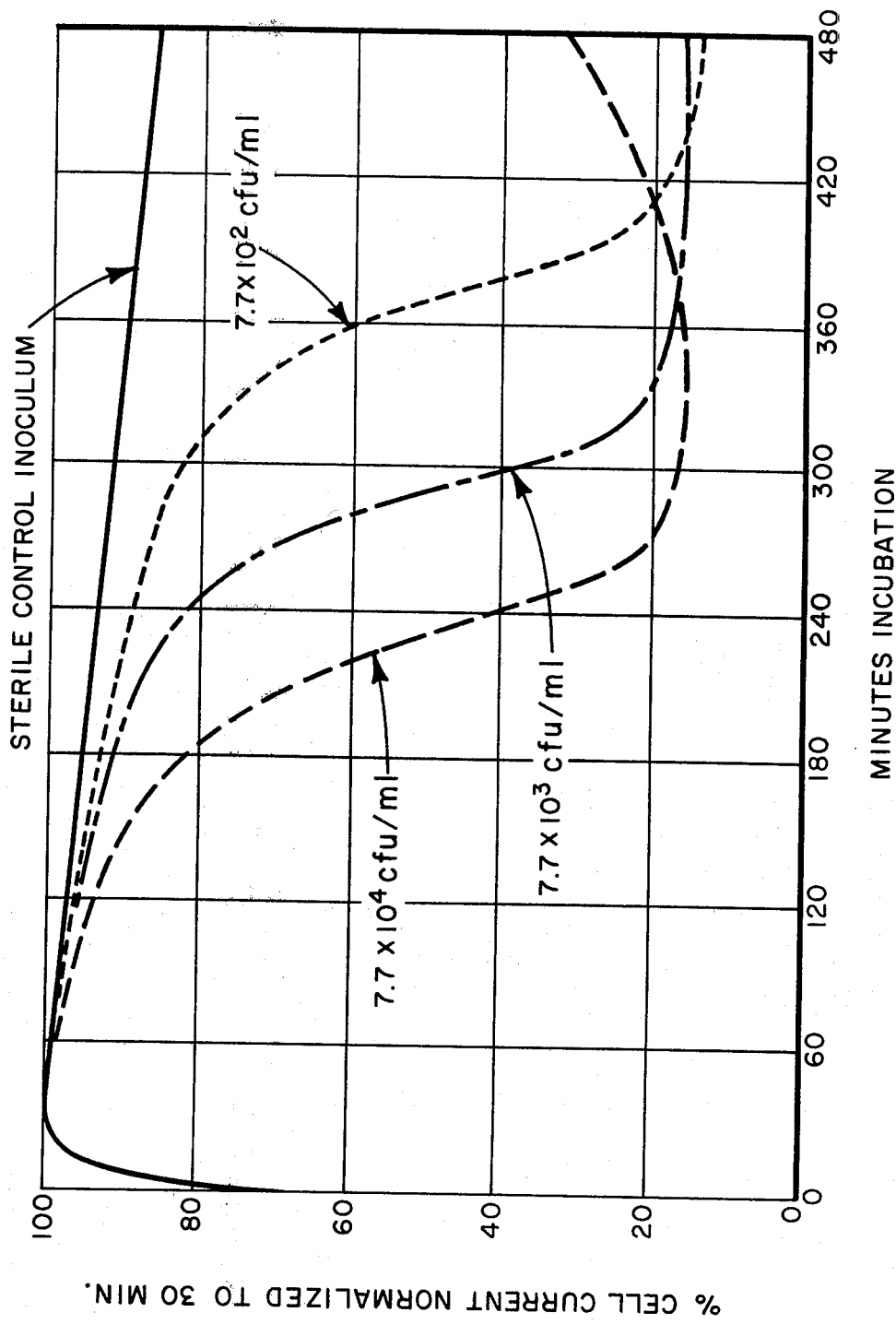
FIG. 18 is a graph showing normalized voltammetric cell current response as a function of incubation time for varying inoculum strengths of the organism *P. aeruginosa*.
Figure 19:
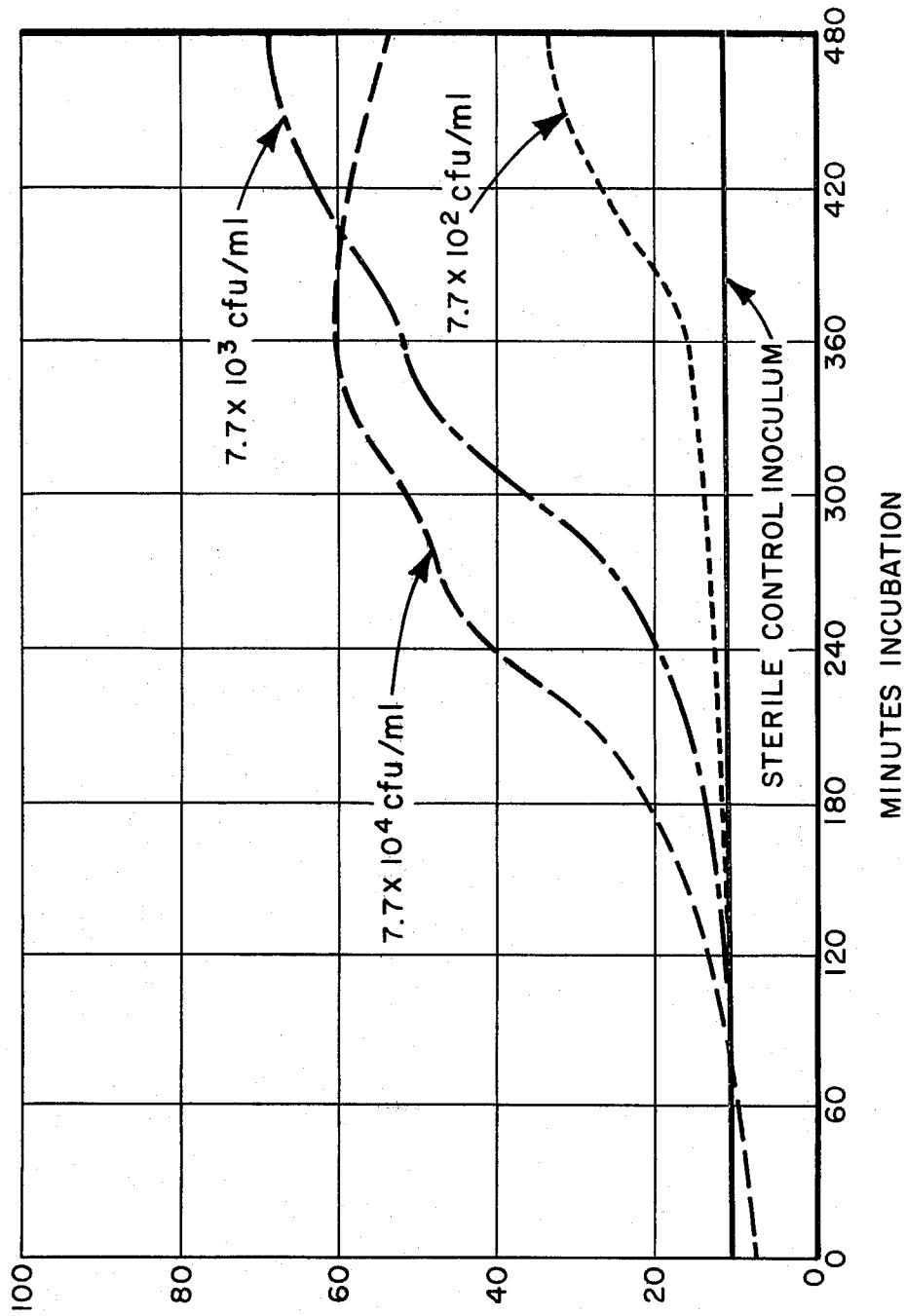
FIG. 19 is a graph showing normalized cell potential response as a function of incubation time for varying inoculum strengths of the organism *P. aeruginosa*.

Cell current response of the organism with decade dilution and of the control cell containing sterile medium are shown in FIG. 18. Normal cell current behavior is observed. The related cell potential responses are presented in FIG. 19. Because *P. aeruginosa* is a relatively slow growing obligate aerobe, cell potential response at each inoculum level changes more slowly and reaches a limiting value of considerably less amplitude than do the facultative anaerobes. Pour plate counts in duplicate were used to determine the initial inoculum level in the ×0.1 cells as $7.7 \times 10^4$ cfu/ml. Times-to-detection for the detection methods are presented in Table 4.

TABLE 4

Times-to-Detection in Minutes for
Cell Current and Cell Potential
for the Organism *P. aeruginosa*

| Initial Inoculum | Cell Current | | Cell Potential | |
|---|---|---|---|---|
| in Cell | A | B | A | B |
| $7.7 \times 10^4$ cfu/ml | 190 | 160 | 220 | 170 |
| $7.7 \times 10^3$ cfu/ml | 220 | 250 | 240 | 310 |
| $7.7 \times 10^2$ cfu/ml | 300 | 310 | 390 | 390 |

EXAMPLE 6

Figure 20:
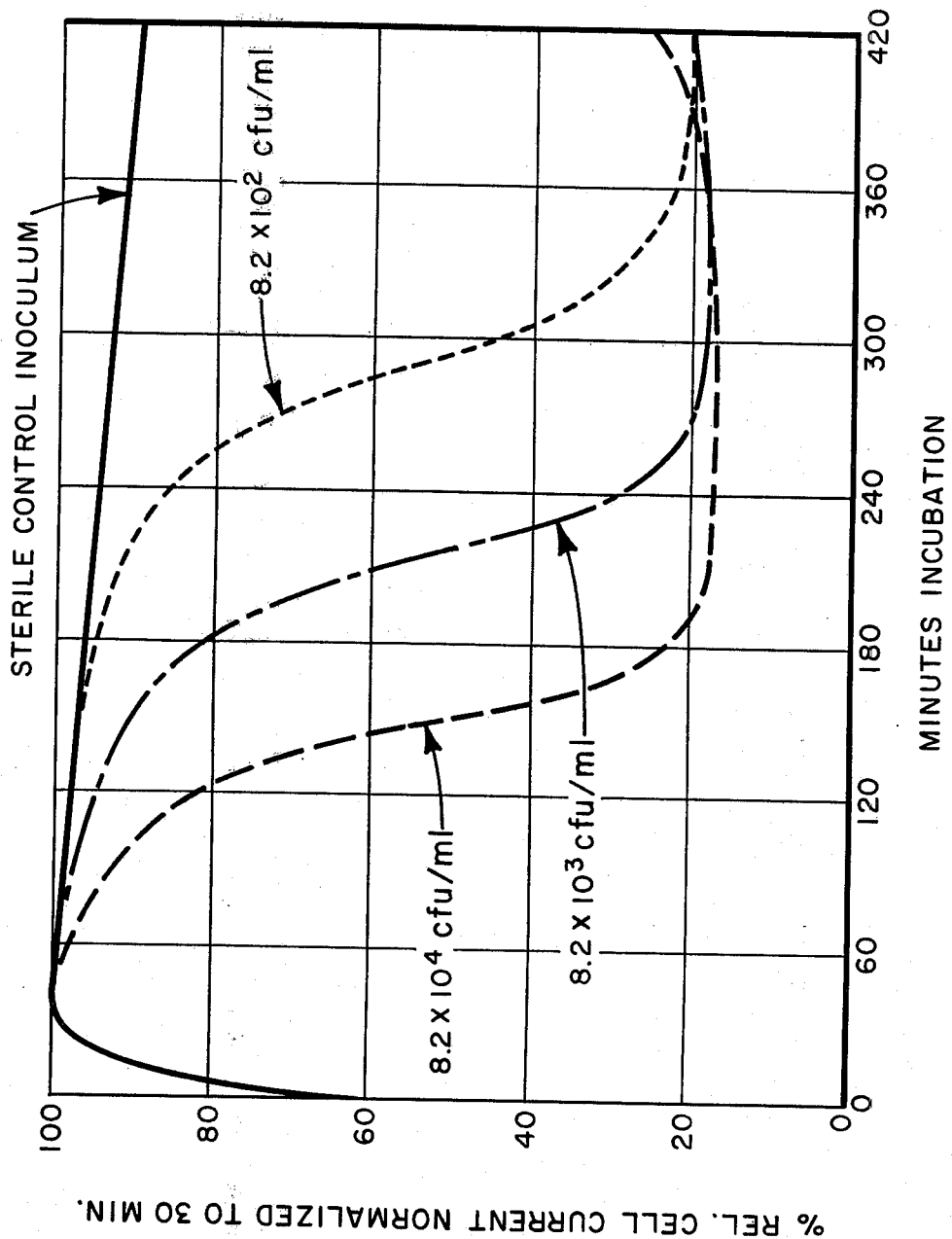
FIG. 20 is a graph showing normalized voltammetric cell current response as a function of incubation time for varying inoculum strengths of the organism *S. aureus*.
Figure 21:
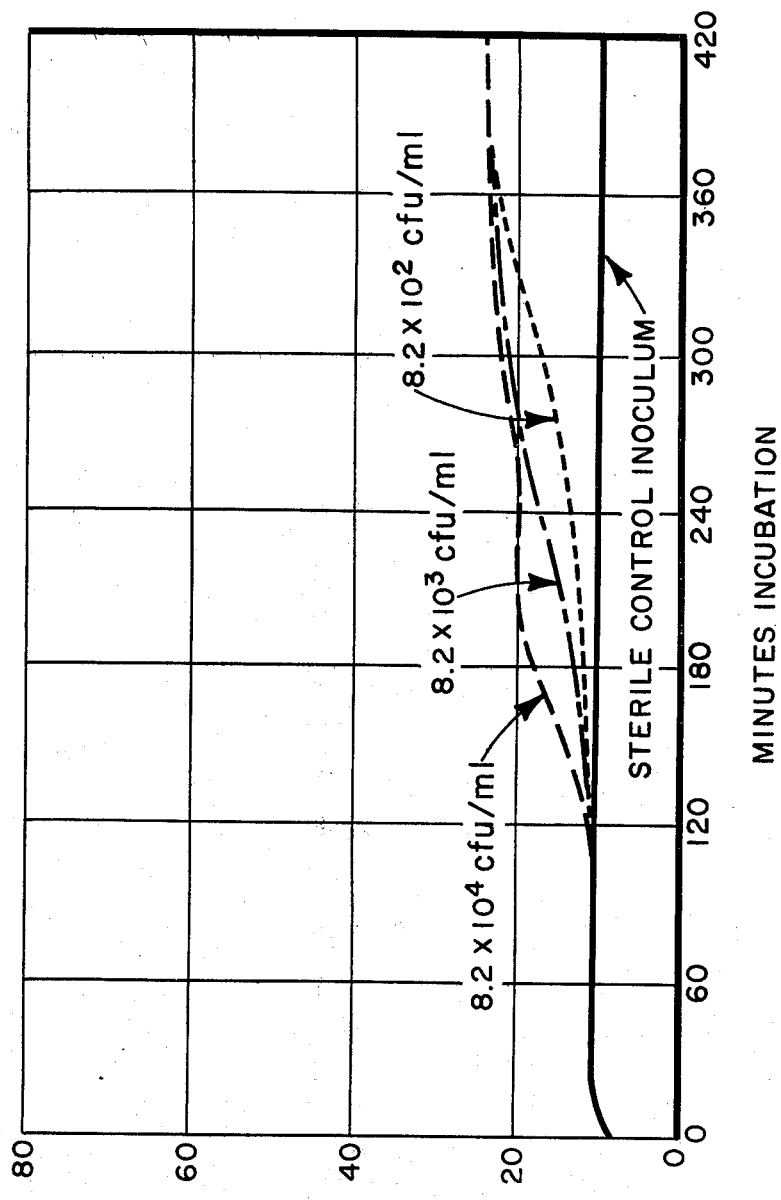
FIG. 21 is a graph showing normalized cell potential response as a function of incubation time for varying inoculum strengths of the organism *S. aureus*.

This example demonstrates the detection and quantification of *S. aureus*. A freshly inoculated vial of 6B medium was incubated overnight at room temperature to serve as the source of all inocula. The sampling and dilution scheme of FIG. 11 was again employed to prepare sample cells and pour plates used in the test. The growth medium in each cell was enriched with 0.1 cc sterile glucose stock solution. All incubations were carried out at 37° C. in a warm-air incubator. Cell current and potential readings were recorded every 10 minutes under computer control. The experiment was continued for 480 minutes (8 hours). Cell current response for the organism at decade inoculum levels is shown in FIG. 20. Normal cell current behavior is obtained. The related cell potential variations are presented in FIG. 21. Note that very little potential change occurs with continued growth of *S. aureus*; threshold detection is barely achieved. Duplicate 24-hour pour plate counts were used to determine the inoculum level in the ×0.1 cells to be $8.2 \times 10^4$ cfu/ml. Times-to-detection for cell current and cell potential methods are given in Table 5.

TABLE 5

Times-to-Detection in Minutes for
Cell Current and Cell Potential
for the Organism *S. aureus*

| Initial Inoculum | Cell Current | | Cell Potential | |
|---|---|---|---|---|
| in Cell | A | B | A | B |
| $8.2 \times 10^5$ cfu/ml | 150 | 130 | 290 | 200 |
| $8.2 \times 10^4$ cfu/ml | 180 | 180 | 250 | 260 |
| $8.2 \times 10^3$ cfu/ml | 250 | 260 | 320 | 340 |

EXAMPLE 7

Figure 22:
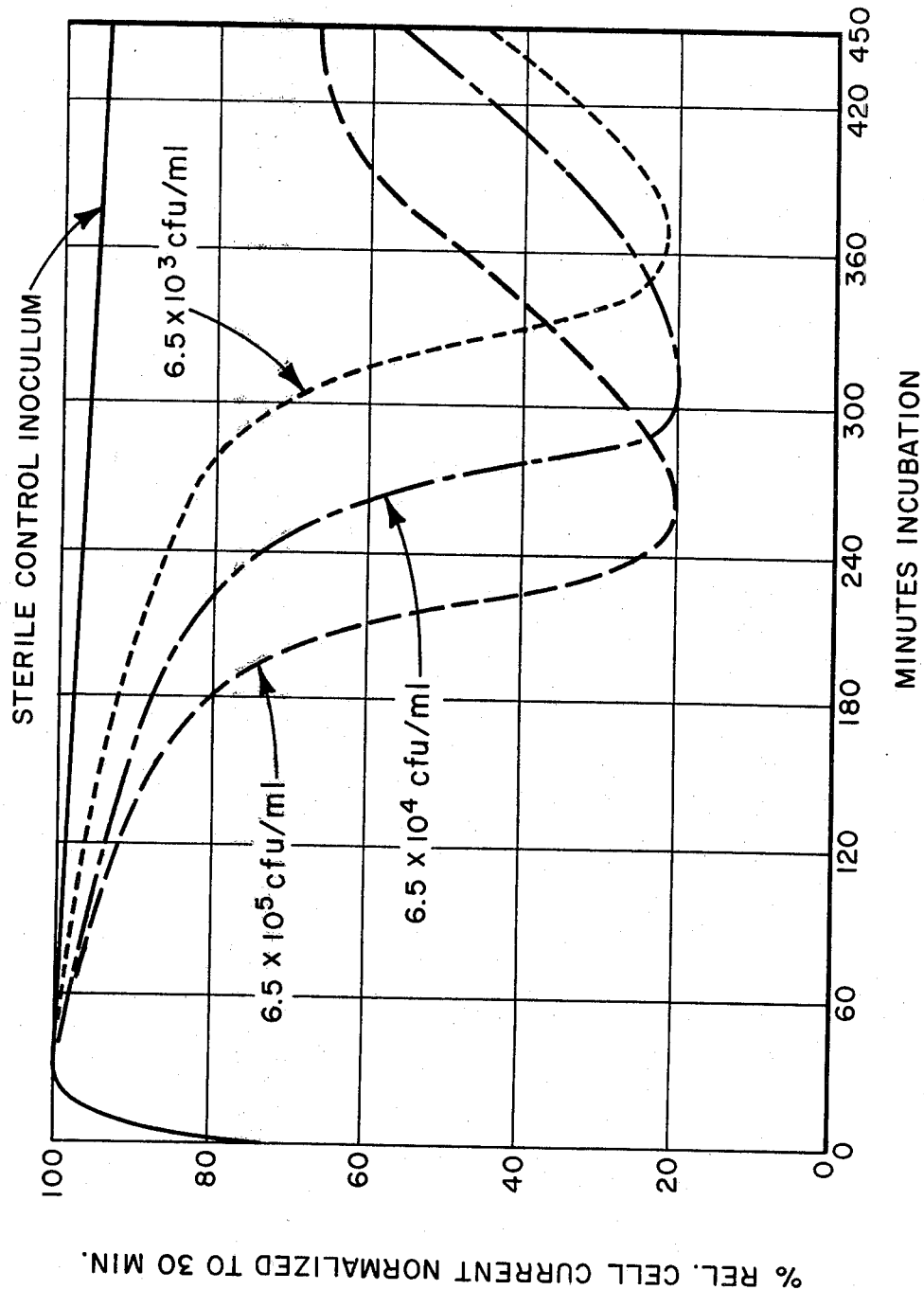
FIG. 22 is a graph showing normalized voltammetric cell current response as a function of incubation time for varying inoculum strengths of the organism *S. bovis*.
Figure 23:
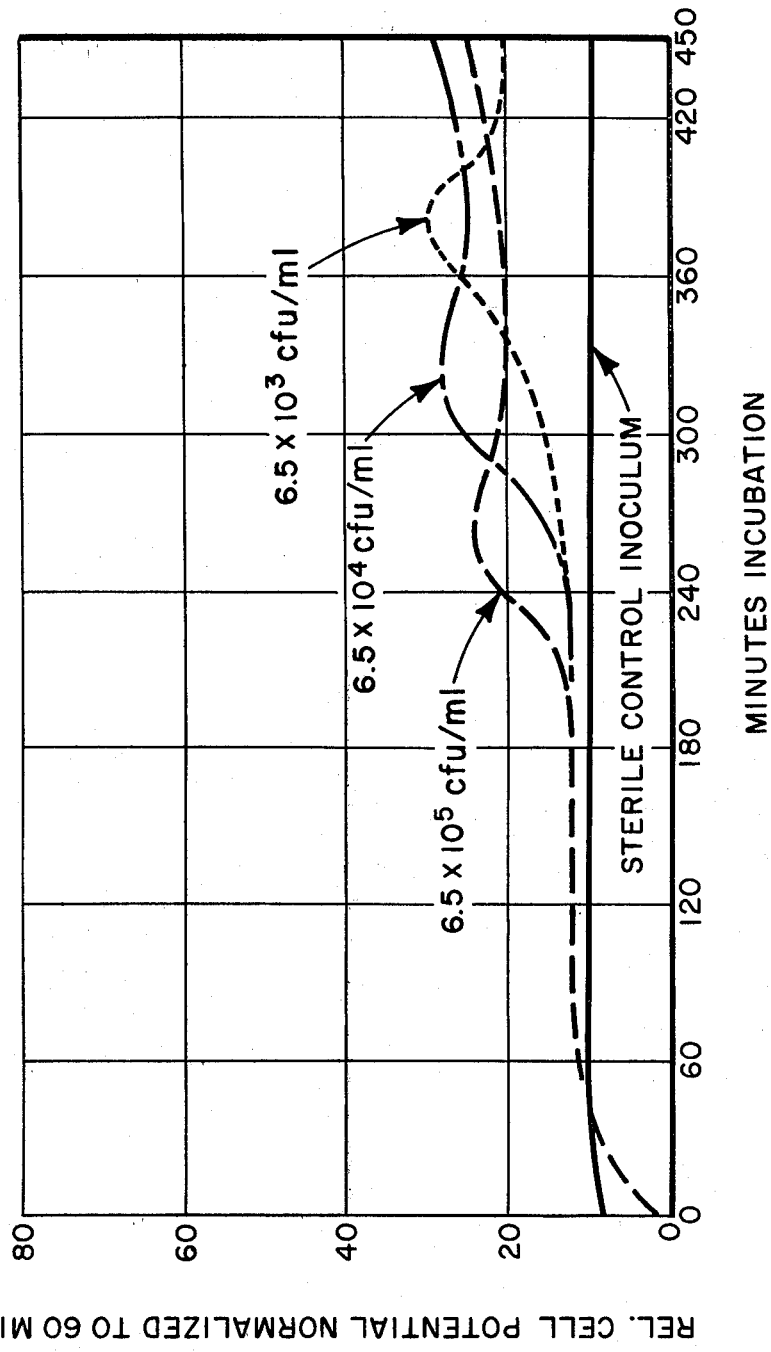
FIG. 23 is a graph showing normalized cell potential response as a function of incubation time for varying inoculum strengths of the organism *S. bovis*.

This example demonstrates the detection and quantifiction of *S. bovis*. A fresh overnight culture of *S. bovis* in 6B medium was used as the inoculum source. Sample cells and pour plates were prepared with reference to FIG. 11. Each cell also received 0.1 cc glucose stock solution as enrichment. All incubations were carried out at 37° C. The measurements were continued for 450 minutes (7½ hours). Cell current measurements are presented in FIG. 22. Normal current response is observed prior to the current minimum at each inoculum level. Values recorded after each minimum rise more rapidly then usual. Cell potential responses are shown in FIG. 23. *S. bovis* causes little change in the potential observed as growth progresses, save for the small singularity usually observed in conjunction with the current minima in FIG. 22. Duplicate 24-hour pour plate counts indicated $6.5 \times 10^5$ cfu/ml to be present in the ×0.1 cells initially. Times-to-detection for the detection methods are presented in Table 6.

TABLE 6

Times-to-Detection in Minutes for
Cell Current and Cell Potential
for the Organism *S. bovis*

| Initial Inoculum | Cell Current | | Cell Potential | |
|---|---|---|---|---|
| in Cell | A | B | A | B |
| $6.5 \times 10^5$ cfu/ml | 200 | 180 | 280 | 240 |
| $6.5 \times 10^4$ cfu/ml | 220 | 220 | 290 | 280 |
| $6.5 \times 10^3$ cfu/ml | 280 | 290 | 330 | 340 |

EXAMPLE 8

This example demonstrates the extended quantification of *E. coli* using pulsed voltammetric detection. A fresh overnight culture of *E. coli* in 6B medium was used as the inoculum source. Dilution vials and pour plates were prepared with reference to FIG. 11, except that dilution vials were prepared out to a dilution ratio of $1:10^6$. The growth medium in each of the cells was enriched with 0.1 cc sterile glucose stock solution. The first seven cells in the 8-cell array each received 1.0 cc from the appropriate dilution vial as inoculum. Cell (8) received 1.0 cc sterile TSB inoculum as the control. Because the cells had previously been mechanically polished and reconditioned, the current sensitivity for this experiment was reduced somewhat to insure that all recorded values would remain within the dynamic range of the A/D converter. Incubation and testing were carried out at 37° C. No preinoculation incubation period was used.

Figure 24:
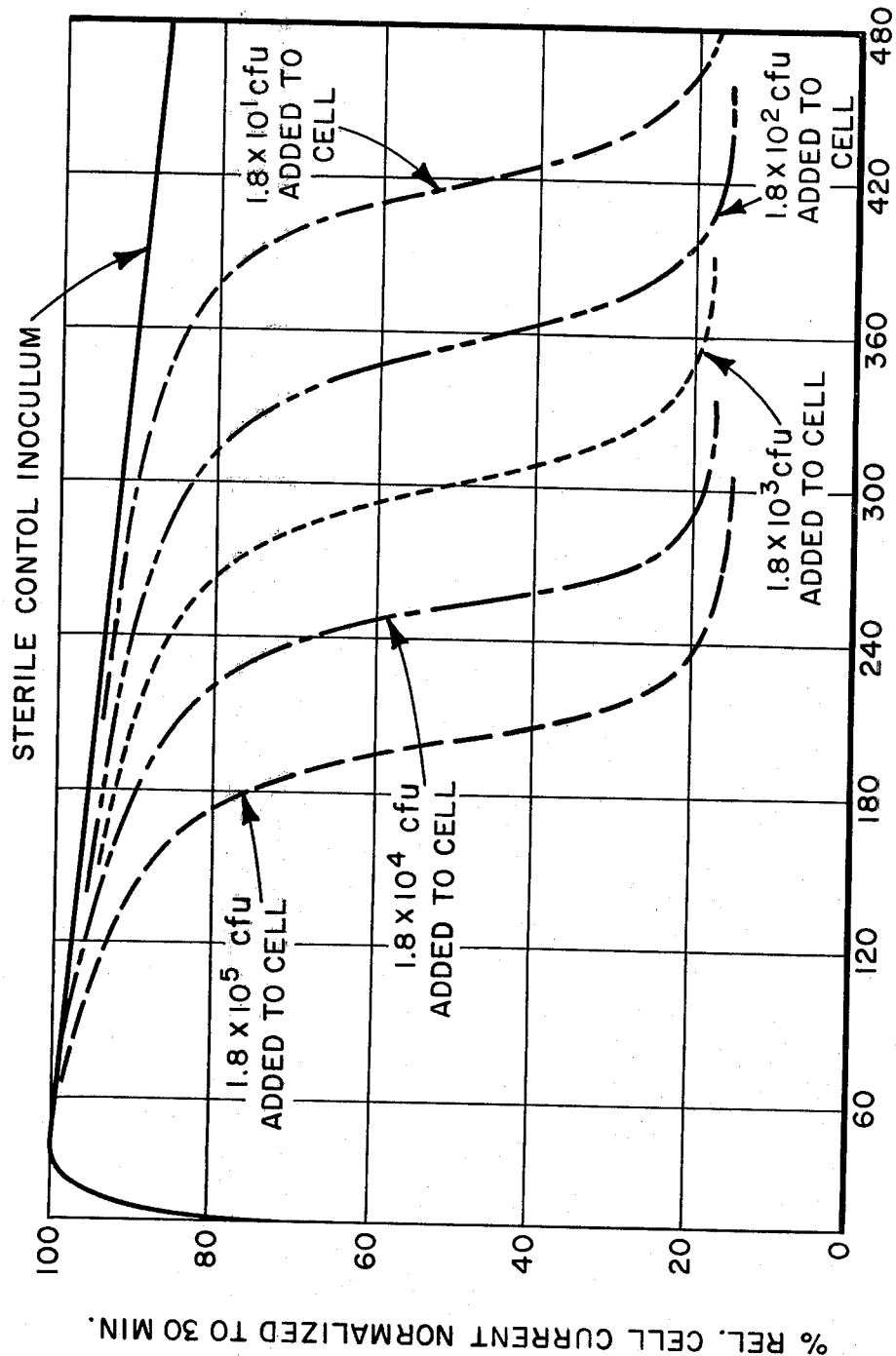
FIG. 24 is a graph showing normalized cell current response as a function of incubation time for the organism *E. coli* with four decades of initial inoculum concentration.
Figure 25:
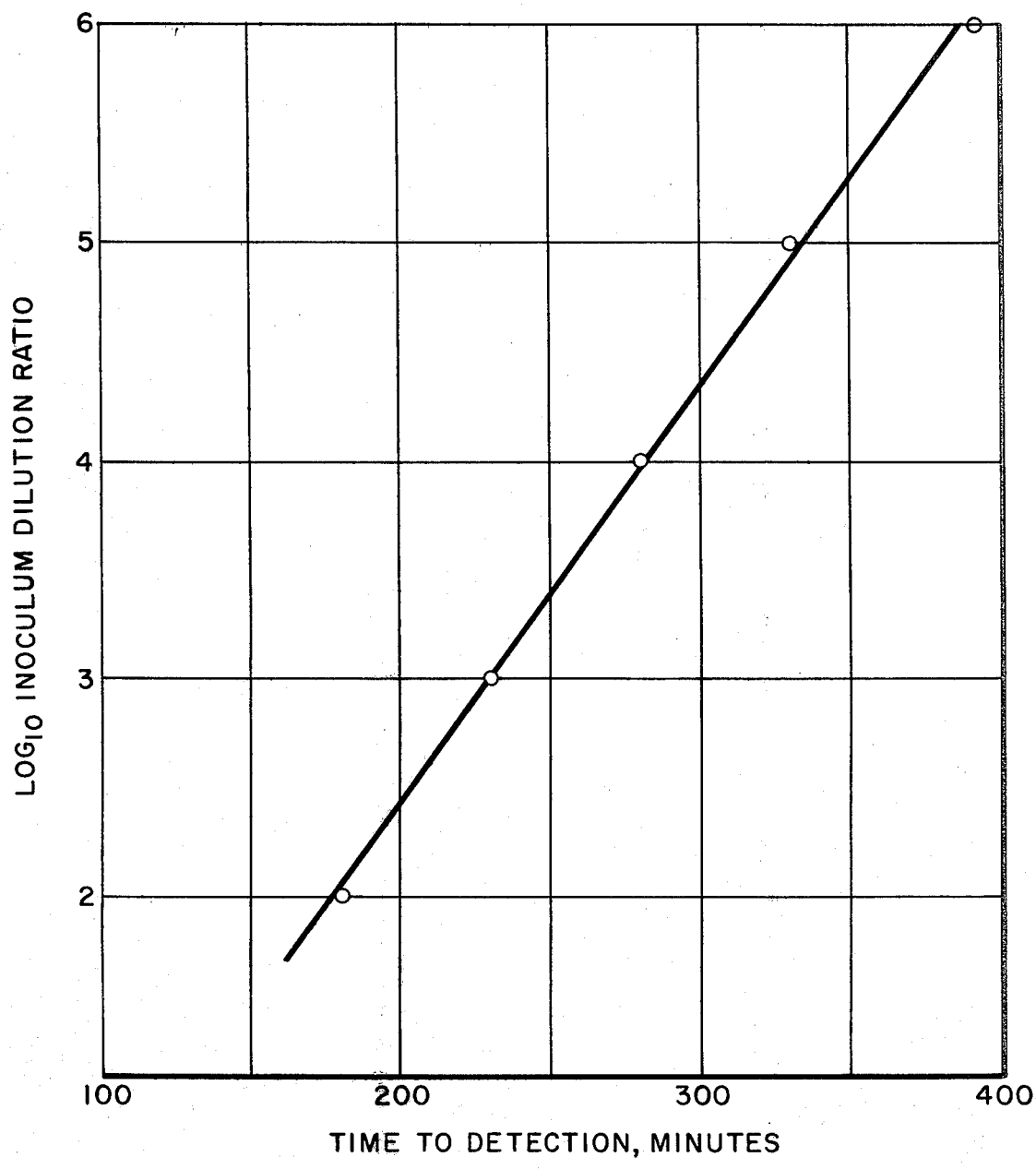
FIG. 25 is a graph showing the logarithm of the initial inoculum dilution ratio as a function of time-to-detection at a 60% detection threshold for the data shown in FIG. 24.

The normalized cell current responses of cells (3) through (8) are shown in FIG. 24. Cell (1) was used as a high-inoculum marker only, since the cell assembly requires at least 30 minutes to attain temperature equilibrium. Cell (2) results were anomalous with respect to detection time, probably due to slight contamination of the cell walls or electrode surfaces during reconditioning, and are not shown. Over the four decades of inoculum level considered, time-to-detection is seen to vary linearly with the logarithm of inoculum strength. Note that the detection threshold has been reduced to 60% of the value observed at the time of normalization; this provides more dependable time-to-detection values in prolonged tests where the slight downward baseline drift with time can generate detection times slightly shorter than the correct values. Note that the B 60% current level occurs near the point of maximum slope of the growth curves. Experience with the system has shown that best quantification when using this technique is obtained when the detection time is taken to be the time at which maximum slope of the growth curve is evidenced. FIG. 25 illustrates the good quantification achieved for inocula of $1.5 \times 10^5$ cfu to $1.8 \times 10^1$ cfu in the present example. Repeated trials with the system has shown that inocula greater than about $5 \times 10^5$ cfu require slightly longer to detect than predicted. This is partly due to the lag induced by the time required for the cell array to reach temperature equilibrium. The remainder of the problem is most likely caused by the finite time required for the organism in question to adapt to the new environment imposed by dilution and sampling. The short time interval between recorded data points (10 minutes) makes even slight deviations from expected behavior noticeable.

EXAMPLE 9

The results for the organisms studies in Examples 2–7 using the 8-cell array (platinum cathode) are summarized in Table 7. Data from parallel radiometric tests (BACTEC) are included for comparison. Cell current duplicate results are shown to differ by a maximum of 30 minutes at any inoculum level for all organisms. Cell potential detection is less reliable for quantification, differing in duplicates by as much as 90 minutes in one case (*S. aureus*).

Pulsed voltammetric detection of the test organisms compares well with detection based upon the BACTEC system; *E. coli* and *E. cloacae* are detected with approximately equal facility by both methods. *P. mirabilis* and most notably, *P. aeruginosa* are detected significantly faster using the cell current measurement. Detection of *S. aureus* by the cell current method is about 40 minutes faster than BACTEC, while *S. bovis detection is accomplished about* 1 hour sooner by the BACTEC system.

Cell potential detection of organism growth compared to either the cell current determination or to the BACTEC system leaves much to be desired. Results can be quite unreliable for organisms such as *S. aureus* (FIG. 21) and *S. bovis* (FIG. 23) which produce little change in solution redox potential with growth. Thresholds for detection are approached slowly and barely exceeded by such organisms as compared to the Enterobacteriacae, thus promoting a test of widely varying sensitivity as a function of the organism being detected. The widely differing redox potential patterns do, however, provide good clues as to the type of organisms simultaneously detected by other means.

TABLE 7

Summary of Results
Times-to-Detection for all Organisms
by All Methods

| Tested Organism | Inoculum Level in Cell or Vial | TIMES-TO-DETECTION, MINUTES | | | | |
|---|---|---|---|---|---|---|
| | | BACTEC | Cell Current | | Cell Potential | |
| | | | A | B | A | B |
| *E. coli* | $1.0 \times 10^5$ cfu/ml | 120 | 120 | 120 | 160 | 180 |
| | $1.0 \times 10^4$ cfu/ml | 180 | 150 | 160 | 220 | 230 |
| | $1.0 \times 10^3$ cfu/ml | 240 | 200 | 200 | 260 | 270 |
| *E. cloacae* | $3.7 \times 10^5$ cfu/ml | 120 | 150 | 150 | 230 | 200 |
| | $3.7 \times 10^4$ cfu/ml | 180 | 210 | 210 | 260 | 240 |
| | $3.7 \times 10^3$ cfu/ml | 240 | 270 | 270 | 300 | 310 |
| *P. mirabilis* | $2.0 \times 10^5$ cfu/ml | 240 | 190 | 170 | 250 | 230 |
| | $2.0 \times 10^4$ cfu/ml | 300 | 220 | 230 | 270 | 280 |
| | $2.0 \times 10^3$ cfu/ml | 420 | 290 | 300 | 340 | 330 |
| *P. aeruginosa* | $7.7 \times 10^4$ cfu/ml | 480 | 190 | 160 | 220 | 170 |
| | $7.7 \times 10^3$ cfu/ml | 600 | 220 | 250 | 240 | 310 |
| | $7.7 \times 10^2$ cfu/ml | 660 | 300 | 310 | 390 | 390 |
| *S. aureus* | $8.2 \times 10^5$ cfu/ml | 180 | 150 | 130 | 290 | 200 |
| | $8.2 \times 10^4$ cfu/ml | 240 | 180 | 180 | 250 | 260 |
| | $8.2 \times 10^3$ cfu/ml | 300 | 250 | 260 | 320 | 340 |
| *S. bovis* | $6.5 \times 10^5$ cfu/ml | 120 | 200 | 180 | 280 | 240 |
| | $6.5 \times 10^4$ cfu/ml | 180 | 220 | 220 | 290 | 280 |
| | $6.5 \times 10^3$ cfu/ml | 240 | 280 | 290 | 330 | 340 |

EXAMPLE 10

This example demonstrates the use of electrodes of other materials and sizes then those used in the foregoing examples. A 6-cell array constructed with 0.020" gold wire as cathode and 0.020" silver wire as anode in each cell was used to test the response of the system toward pulse voltammetric detection only. The gold cathode prevented collection of potential data, but gold is somewhat less expensive then platinum to use in cases where detection alone will suffice. The gold and silver wires, arranged in parallel fashion in the bottom of each cell, were each 1.4 cm long and were separated by 1.6 cm. The observed cell currents were appreciably lower than those observed when using the 8-cell array with larger diameter wires and platinum cathode. No attempt was made to measure true current sensitivity. The cells were prepared with either 1.5 cc or 2.0 cc TSA and 5.0 cc enriched 6B medium, and were tested with various organisms under the same conditions as for the previously noted experiments. No electrode pretreatment was employed. The pulse amplitude (−0.70 V) and the pulse duration (1200 ms) were the same as in the previous examples. Duplicate pour plates were also prepared for these experiments. Cell current data normalization was carried out as previously described. Fresh overnight cultures of *E. coli, P. mirabilis,* and *P. aeruginosa* in 6B medium were used as inoculum sources. All sample and pour plate preparations were preformed with reference to FIG. 11. Cell current readings were obtained at 10-minute intervals. No pre-inoculation incubation was employed.

Figure 26:
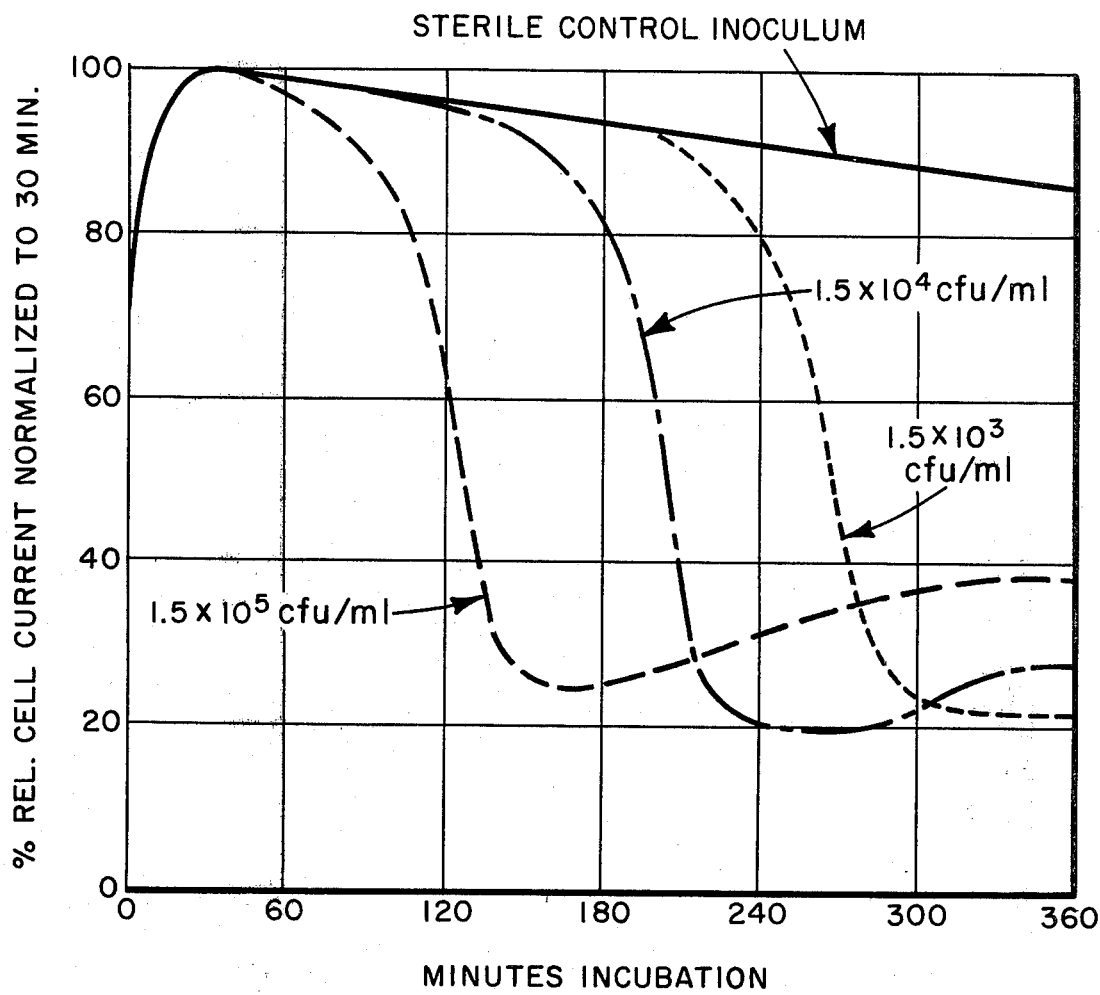
FIG. 26 is a graph showing normalized voltammetric cell current response as a function of incubation times for varying inoculum strengths of the organism *E. coli* using cells fitted with gold cathodes.
Figure 27:
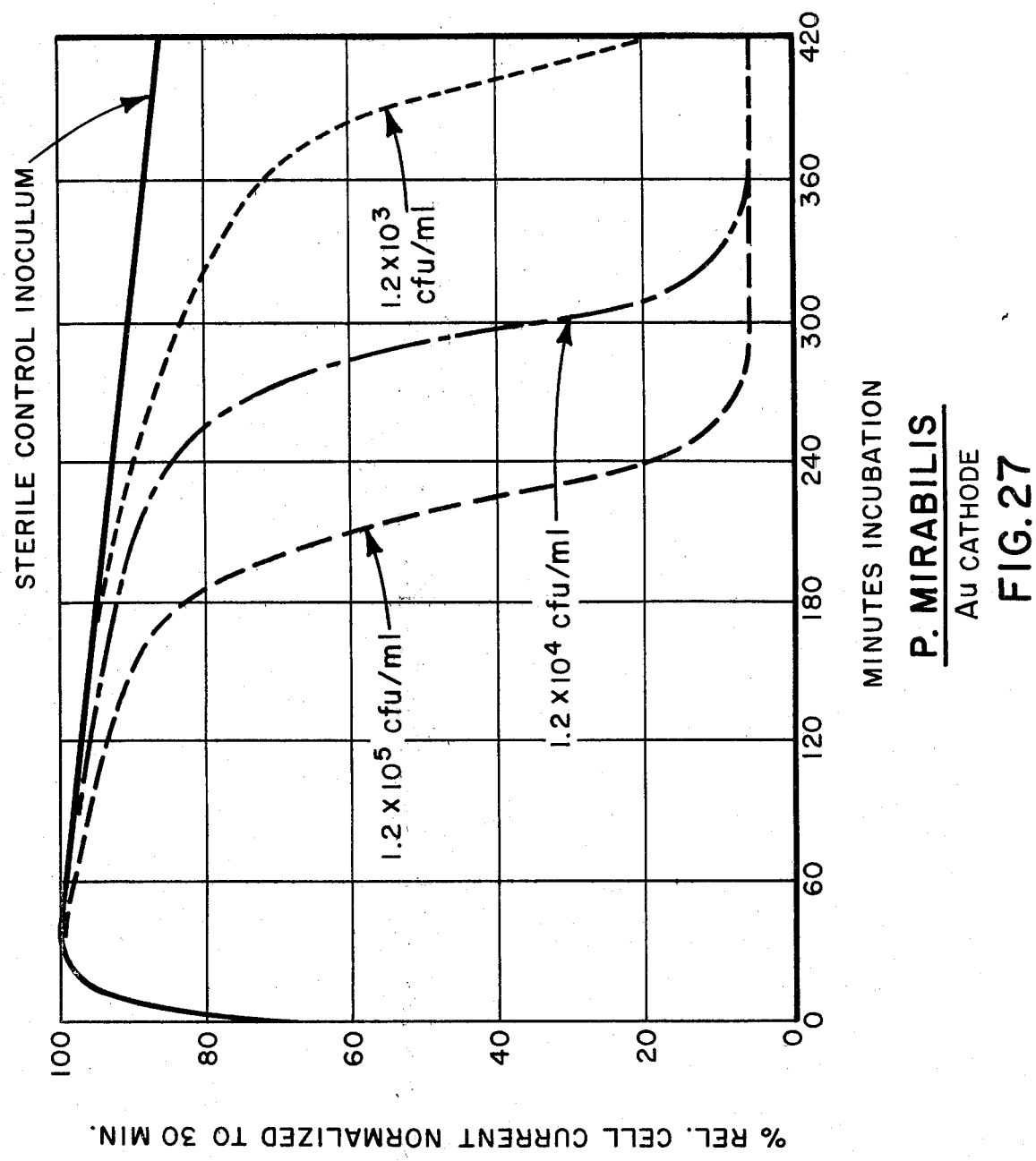
FIG. 27 is a graph showing normalized voltammetric cell current response as a function of incubation times for varying inoculum strengths of the organism *P. mirabilis* using cells fitted with gold cathodes.
Figure 28:
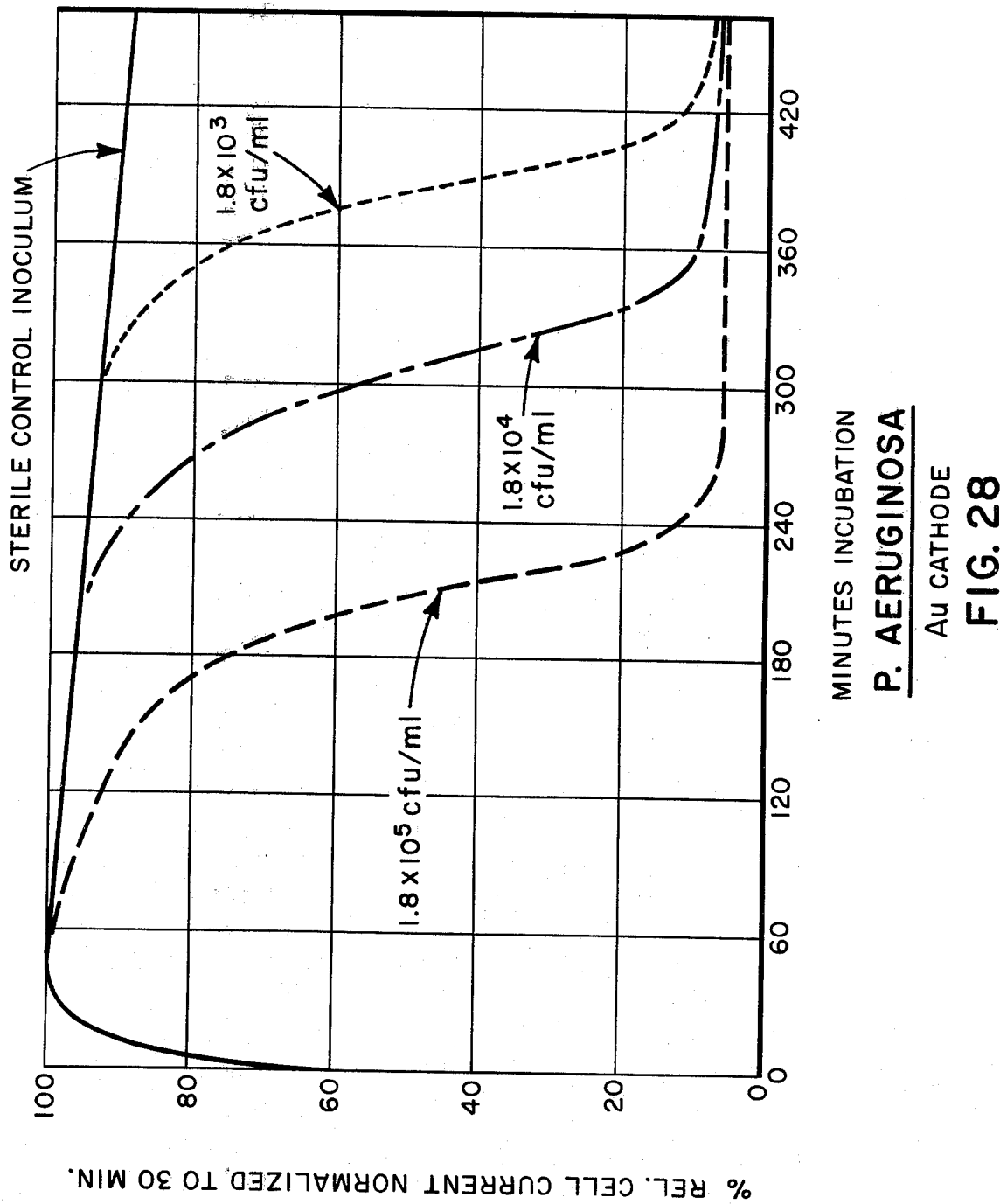
FIG. 28 is a graph showing normalized voltammetric cell current response as a function of incubation times for varying inoculum strengths of the organism *P. aeruginosa* using cells fitted with gold cathodes.
Figure 29:
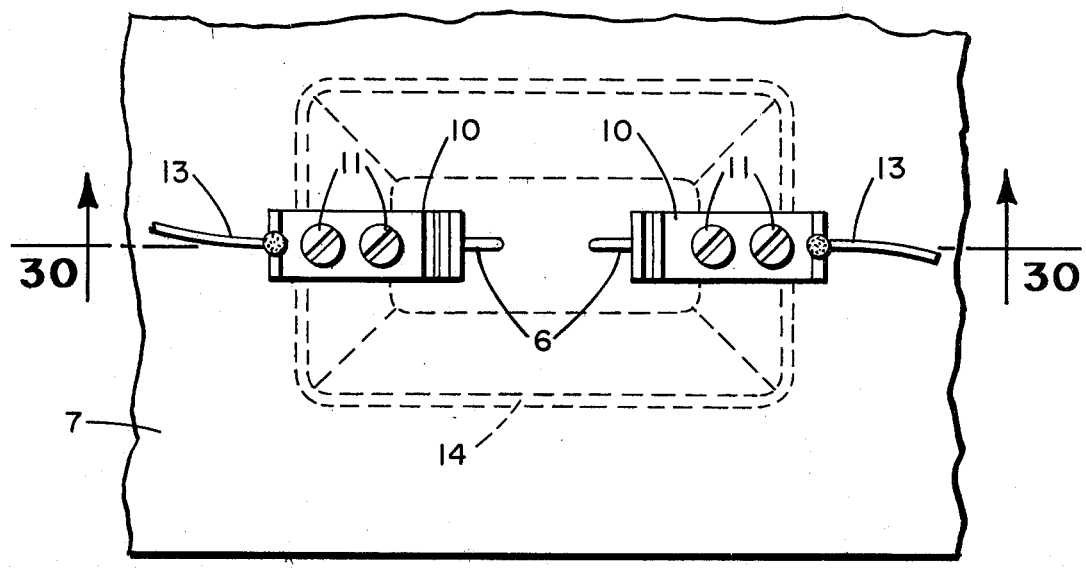
FIG. 29 is a top plan view of another electroanalytical cell useful in the practice of the present invention.
Figure 30:
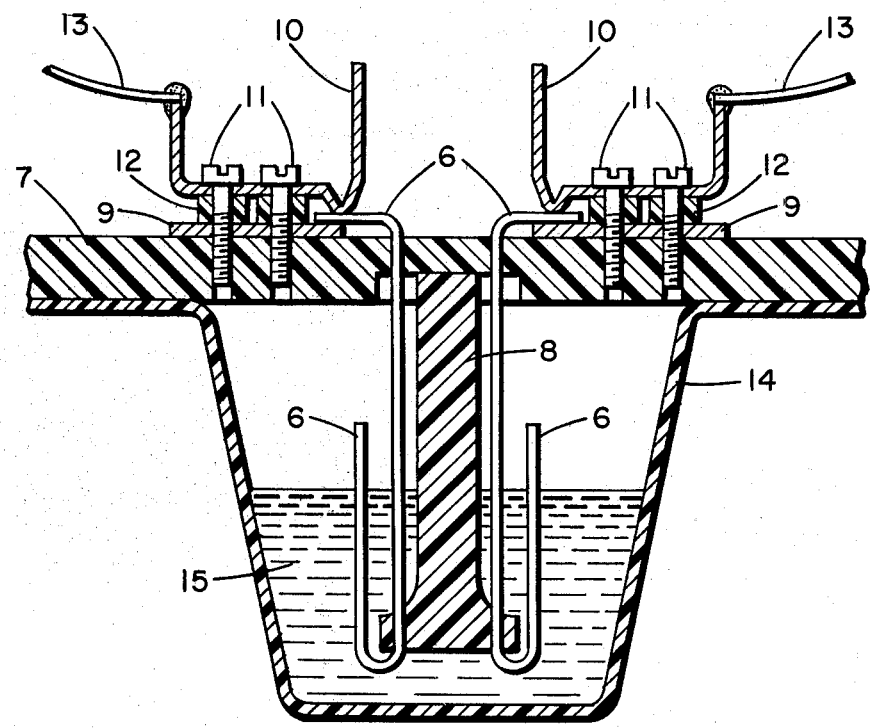
FIG. 30 is a sectional view of the electroanalytical cell of FIG. 29 taken along line 30—30.

Results obtained for separate tests using *E. coli, P. mirabilis* and *P. aeruginosa* are shown in FIGS. 26, 27 and 28, respectively. The organism inoculum level for the most concentrated cell in each experiment is listed below:

| | |
|---|---|
| E. coli | $1.5 \times 10^5$ cfu/ml |
| P. mirabilis | $1.2 \times 10^5$ cfu/ml |
| P. aeruginosa | $1.8 \times 10^5$ cfu/ml |

The other tracings in each Figure are for decade dilutions and a sterile control cell. In all cases, detection of the organism was readily accomplished, as indicated by a drop in recorded cell current to 80% of the normalization value. Times-to-detection for all dilutions in each of the figures are seen to depend upon the inoculum level in a predictable manner, varying essentially as the logarithm of inoculum concentration. The slight scatter noted in some of the data is due to stray pickup by the analog conditioning electronics; a capacitor was added across the voltage-to-current conversion operational amplifier to alleviate this problem. Downward baseline drift noted for the control samples is most likely due to the lack of any preconditioning of the cells. Any increase in times-to-detection noted at a given inoculum level of a specific organism when using the 6-cell array is probably a function of the thickness of TSA over the electrodes, particularly in the case where 2.0 cc was used. Once the electrodes are covered, detection times increase as the level of TSA in the cell increases as a consequence of the increased diffusion path. 2.0 cc TSA was used in the experiment run with *P. aeruginosa*. The *E. coli* and *P. mirabilis* experiments both used 1.5 cc TSA.

EXAMPLE 11

This example demonstrates a clinical trial of the pulsed voltammetric detection technique of the present inventor for the detection of significant bacteriuria. The test was conducted in conjunction with Sinai Hospital of Baltimore. Over the 33-day period of the study, 389 urine samples were collected from Sinai and tested at Johnston Laboratories using the pulsed voltammetric technique in parallel with the BACTEC radiometric system. TSA pour plates were employed to check actual organism counts.

The test was carried out as follows. Urine specimens sampled following Sinai collection and planting were picked up from the hospital at approximately 11:00 AM each day. Prior to sample arrival at JLI, the 16-cell assembly to be used with the Pulsed Voltammetric instrumentation was filled with scalding hot water and allowed to stand for at least ten minutes. The assembly was then rinsed twice with sterile deionized water, then shaken vigorously to dislodge any large water droplets. 1.0 cc sterile Tryptic Soy Agar (40.0 g/l; BBL or DIFCO) at about 95° C. was then added by sterile syringe to each cavity of the assembly. The assembly was then covered with a double thickness of aluminum foil sterilized with isopropanol, and the agar allowed to solidify. 5.0 cc of sterile TSB (27.5 g/l; BBL or DIFCO) containing Dextrose (2.5 g/l; MALLINCKRODT or J. T. BAKER) was then added to each cavity via syringe, and the cover replaced.

Upon arrival at JLI, urine samples were cataloged as to JLI daily and consecutive sequence numbers, Sinai reference number, and gross physical characteristics. 1.0 cc of each urine specimen was inoculated via syringe into one cell of the assembly. Similarly, 1.0 cc was used to inoculate a septum-fitted vial of nominal 50 cc capacity containing 5.0 cc of JLI 4A Urine Screening Medium (JLI B/N 037901U-1.5uCi/vial) for use in the parallel BACTEC study. 0.1 cc of each specimen was inoculated into previously refrigerated, septum-fitted vials containing 99.9 cc ½-strength TSB to obtain 1:1000 sample dilution for the pour plate studies. Plates were prepared at $1:10^3$ and $1:10^4$ dilutions for each sample using 10–15 ml TSA (40.0 g/l) and 1.0 cc and 0.1 cc from each dilution vial, respectively.

The inoculated cell assembly was placed in a 37° C. warm air incubator without agitation and pulsed voltammetric testing begun under computer control. Test values were recorded for all samples at 10-minute intervals. Data normalization was based upon sample data values recorded after the first 10 minutes for tabulation; all data values recorded for each sample were ultimately expressed as a percentage of the 10-minute value. A sample was considered to be positive when the normalized data value for that sample at any given time interval after normalization fell below 70 or rose above 140. The latter criterion was employed to permit detection of some highly positive (ca. $10^8$ cfu/ml) samples which produced data minima slightly greater than 70, yet which interfered with normal operation sufficiently to produce data maxima over 140.

Each day of testing concluded with the generation of a computer printout which included plots of relative cell potential readings, and a table of normalized cell current readings for each sample, all as a function of incubation time. The normalized, tabulated results were used to determine sample result classifications.

Of the 389 tested samples, 45 were omitted from the study usually for experimental reasons (Incubator Failure, 12; Cell Reconditioning Failure, 14; Contaminated Petri Dishes, 12; JLI/Hospital Data Discrepancy, 7). Contaminated samples numbered 30, and were similarly omitted from further consideration. Of the remaining 314 samples, 84 were considered significant clinically. Table 8 lists the organisms identified by Sinai Hospital found to be present in the significant samples. The number of samples containing each organism is also noted, as is the percentage of the total containing that organism. Non-integer sample numbers are due to samples containing more than one organism.

TABLE 8

| Organisms Contributing to Significant Samples | | |
|---|---|---|
| Organism | No. of Samples | Percentage |
| E. coli | 34.5 | 41.07 |
| P. aeruginosa | 10.5 | 12.50 |
| K. pneumoniae | 9.0 | 10.71 |
| P. mirabilis | 6.0 | 7.14 |
| Yeast, unspecified | 3.5 | 4.17 |
| S. aureus | 3.0 | 3.57 |
| C. albicans | 2.5 | 2.98 |
| Grp. B, Beta Strep | 2.5 | 2.98 |
| Grp. D Strep | 2.0 | 2.38 |
| S. albus | 2.0 | 2.38 |
| K. oxytoca | 1.5 | 1.79 | control is presented in FIG. 32. Times-to-detection at the 80% threshold are seen to vary in a predictable manner as a function of inoculum strength. Duplicate pour plate results indicate that 1.4×10E5 cfu/ml *E. coli* were present in the ×0.1 well. Detection times and inoculum levels for all wells are given below:

| Inoculum Level | Detection Time |
| --- | --- |
| 1.4 × 10E5 | 150 minutes |
| 1.4 × 10E4 | 210 minutes |
| 1.4 × 10E3 | 300 minutes |

EXAMPLE 13

A fresh overnight culture of *E. cloacae* in 6B medium was used as the source for all inocula. The sampling and dilution scheme presented in FIG. 11 was used to prepare sample cells and pour plates. Tryptic soy broth with dextrose (30.0 g/l) was used as the growth medium for detection. All incubations were performed at 37 degrees C. Cell readings were continued for 7 hours.

The cell current response for each of the three decade dilutions of *E. cloacae* plus control is shown in FIG. 33. Detection time is observed to vary predicatably with the level of inoculum in each well. Pour plates prepared at the time of inoculation showed the ×0.1 well to contain 2.2×10E5 cfu/ml of the organism. Inoculum levels and associated detection times for all wells are given below:

| Inoculum Level | Detection Time |
| --- | --- |
| 2.2 × 10E5 | 170 minutes |
| 2.2 × 10E4 | 250 minutes |
| 2.2 × 10E3 | 320 minutes |

EXAMPLE 14

A fresh overnight culture of *P. aeruginosa* in 6B medium was used as the inoculum source. Once again, the sampling and dilution scheme presented in FIG. 11 was used to prepare sample wells and pour plates for the experiment. TSB with dextrose (30.0 g/l) was used as the growth medium and electrolyte for the study. All incubations were performed at 37 degrees C. Cell readings were taken under computer control for 8 hours.

The cell current response normalized at the 20-minute interval for the three decade dilutions of the organism is presented in FIG. 34. Detection time at the 80% threshold is seen to vary in a predictable manner with the level of initial inoculum. Duplicate pour plate results indicate that 1.4×10E5 cfu/ml *P. aeruginosa* was present in the ×0.1 well at the time of inoculation. Each inoculum level and like time-to-detection is presented below:

| Inoculum Level | Detection Time |
| --- | --- |
| 1.4 × 10E5 | 210 minutes |
| 1.4 × 10E4 | 320 minutes |
| 1.4 × 10E3 | 420 minutes |

The technique of the present invention is thus shown to provide competent detection of significant bacteriuria, with clinically acceptable levels of false negative and false positive results. The rapidity and sensitivity of the method compare favorably with parallel results obtained using the BACTEC system.

While certain specific embodiments of the invention has been described with particulars herein, it should be recognized that various modifications thereof will occur to those skilled in the art. Therefore, the scope of the invention is to be limited solely by the scope of the claims appended hereto.

I claim:

1. An electroanalytical method for detecting the presence of oxygen-consuming microorganisms in a sample comprising the steps of:
   (a) providing a mixture of said sample and a fluid culture medium capable of supporting microorganism growth in an electroanalytical cell equipped with two electrodes which are in contact with said mixture;
   (b) applying a series of voltage pulses of substantially constant amplitude and duration across said electrodes; and
   (c) measuring the resulting current through said cell prior to the trailing edge of each of said applied voltage pulses;
   the presence of oxygen-consuming microorganisms being indicated by a decrease in cell current which is a function of the dissolved oxygen content of said mixture.

2. The method of claim 1 additionally comprising the measurement of the open-cell oxidation-reduction potential across said electrodes during the interval between successive applied voltage pulses.

3. The method of claim 1 or 2 wherein said voltage pulses have an amplitude of from about −0.35 v. to about −0.90 v.

4. The method of claim 3 wherein said voltage pulses have a duration of at least about 600 milliseconds.

5. The method of claim 1 or 2 wherein said voltage pulses have a duration of at least about 600 milliseconds.

6. The method of claim 5 wherein said voltage pulses have a duration of about 1200 milliseconds.

7. The method of claim 1 or 2 wherein said voltage pulses are separated by an interval of about 5 to 20 minutes.

8. The method of claim 1 wherein the cathode in said electroanalytical cell is made from a noble metal.

9. The method of claim 8 wherein said cathode is made from platinum, gold or silver.

10. The method of claim 2 wherein said cathode in said electroanalytical cell is platinum.

11. The method of claim 1 or 2 wherein the reference electrode in said electroanalytical cell is silver/silver oxide or silver/silver chloride.

12. The method of claims 1 or 2 wherein said electrodes are covered with a conductive porous gel.

13. The method of claim 12 wherein said gel is a nurient gel.

14. The method of claim 13 wherein said nutrient gel is tryptic soy agar.

15. The method of claims 1 or 2 wherein said electroanalytical cell and its contents are maintained in a constant temperature environment during said measuring.

16. The method of claim 15 wherein said cell is maintained at about 37° C.

17. The method of claims 1 or 2 wherein said fluid culture medium comprises tryptic soy broth.

* * * * *